(12) United States Patent
Pearson et al.

(10) Patent No.: US 8,188,203 B2
(45) Date of Patent: May 29, 2012

(54) COPOLYMERIZABLE AZO COMPOUNDS AND ARTICLES CONTAINING THEM

(75) Inventors: Jason Clay Pearson, Kingsport, TN (US); Max Allen Weaver, Kingsport, TN (US); Jean Caroll Fleischer, Kingsport, TN (US)

(73) Assignee: Abbott Medical Optics Inc., Santa Ana, CA (US)

( * ) Notice: Subject to any disclaimer, the term of this patent is extended or adjusted under 35 U.S.C. 154(b) by 573 days.

(21) Appl. No.: 12/026,294

(22) Filed: Feb. 5, 2008

(65) Prior Publication Data

US 2008/0182957 A1 Jul. 31, 2008

Related U.S. Application Data

(62) Division of application No. 11/271,344, filed on Nov. 10, 2005, now Pat. No. 7,326,423.

(51) Int. Cl.
*C08F 226/06* (2006.01)
(52) U.S. Cl. ..................... 526/263; 526/303.1; 526/309; 526/316
(58) Field of Classification Search .................. 526/263, 526/303.1, 309, 316
See application file for complete search history.

(56) References Cited

U.S. PATENT DOCUMENTS

| | | |
|---|---|---|
| 4,304,895 A | 12/1981 | Loshaek |
| 4,390,676 A | 6/1983 | Loshaek |
| 4,528,311 A | 7/1985 | Beard et al. |
| 4,617,374 A | 10/1986 | Pruett et al. |
| 4,636,212 A | 1/1987 | Posin et al. |
| 4,681,412 A | 7/1987 | Lemelson |
| 4,716,234 A | 12/1987 | Dunks et al. |
| 4,737,322 A | 4/1988 | Bruns et al. |
| 4,753,654 A | 6/1988 | Posin et al. |
| 4,863,466 A | 9/1989 | Schlegel |
| 4,929,250 A | 5/1990 | Hung et al. |
| 4,955,904 A | 9/1990 | Atebara et al. |
| 4,963,160 A | 10/1990 | Hung et al. |
| 4,998,817 A | 3/1991 | Zeltzer |
| 5,008,102 A | 4/1991 | York |
| 5,047,447 A | 9/1991 | Gallas |
| 5,098,445 A | 3/1992 | Hung et al. |
| 5,120,120 A | 6/1992 | Cohen |
| 5,172,256 A | 12/1992 | Sethofer et al. |
| 5,235,358 A | 8/1993 | Mutzhas et al. |
| 5,269,813 A | 12/1993 | Yoshida et al. |
| 5,272,151 A | 12/1993 | Marzi et al. |
| 5,298,033 A | 3/1994 | Hung et al. |
| 5,374,663 A | 12/1994 | Daicho et al. |
| 5,376,650 A | 12/1994 | Weaver et al. |
| 5,399,692 A | 3/1995 | Hung et al. |
| 5,470,932 A | 11/1995 | Jinkerson |
| 5,500,024 A | 3/1996 | Hung et al. |
| 5,528,322 A | 6/1996 | Jinkerson |
| 5,534,041 A | 7/1996 | Havens et al. |
| 5,543,504 A | 8/1996 | Jinkerson |
| 5,657,726 A | 8/1997 | Diggs |
| 5,662,707 A | 9/1997 | Jinkerson |
| 5,846,457 A | 12/1998 | Hoffman |
| 5,866,635 A | 2/1999 | Collins et al. |
| 5,922,246 A | 7/1999 | Matsushita et al. |
| 6,143,028 A | 11/2000 | Galin et al. |
| 6,158,862 A | 12/2000 | Patel et al. |
| 6,187,042 B1 | 2/2001 | Sheets, Jr. et al. |
| 6,224,210 B1 | 5/2001 | Chateau et al. |
| 6,242,551 B1 | 6/2001 | Tsuzuki et al. |
| 6,244,707 B1 | 6/2001 | Faubl |
| 6,277,940 B1 | 8/2001 | Niwa et al. |
| 6,280,471 B1 | 8/2001 | Peyman et al. |
| 6,305,801 B1 | 10/2001 | Kerns, Jr. et al. |
| 6,310,215 B1 | 10/2001 | Iwamoto |
| 6,326,448 B1 | 12/2001 | Ojio et al. |
| 6,387,127 B1 | 5/2002 | Muller-Lierheim |
| 6,399,805 B2 | 6/2002 | Wolf et al. |
| 6,432,137 B1 | 8/2002 | Nanushyan et al. |
| 6,604,824 B2 | 8/2003 | Larson |
| 7,098,283 B2 | 8/2006 | Lai |
| 7,232,896 B2 | 6/2007 | Miki et al. |
| 7,241,312 B2 | 7/2007 | Lai et al. |
| 7,278,737 B2 | 10/2007 | Mainster et al. |
| 7,677,725 B2 | 3/2010 | Piers et al. |
| 2002/0042653 A1 | 4/2002 | Copeland et al. |
| 2002/0082312 A1 | 6/2002 | Lai |
| 2003/0078359 A1* | 4/2003 | Ichinohe .................. 528/25 |
| 2003/0144733 A1 | 7/2003 | Brady et al. |
| 2005/0143812 A1 | 6/2005 | Paul et al. |
| 2006/0115516 A1 | 6/2006 | Pearson et al. |

FOREIGN PATENT DOCUMENTS

| | | |
|---|---|---|
| DE | 3428895 A1 | 2/1986 |
| EP | 161765 B1 | 10/1988 |
| EP | 485197 A1 | 5/1992 |
| EP | 488145 A2 | 6/1992 |
| EP | 359829 B1 | 11/1993 |
| EP | 1043365 A1 | 10/2000 |
| EP | 1030194 B1 | 12/2002 |
| EP | 1293541 A2 | 3/2003 |
| FR | 2622984 A1 | 5/1989 |
| JP | 1501172 T | 4/1989 |
| JP | 1204668 A | 8/1989 |
| JP | 6072151 A | 3/1994 |

(Continued)

OTHER PUBLICATIONS

European Search Report for Application No. EP10181919, mailed on Nov. 3, 2010, 2 pages.
International Search Report for Application No. PCT/US2005/41075, mailed on Jul. 17, 2006, 4 pages.
Office Action mailed Aug. 2, 2011 for Japanese Application No. 2007543145.

*Primary Examiner* — Edward J Cain
(74) *Attorney, Agent, or Firm* — Abbott Medical Optics Inc.

(57) ABSTRACT

Polymerizable light absorbing azo dyes are disclosed useful as monomers in the formation of devices such as, but not limited to ocular lenses. Specifically, intraocular lenses (IOL) are disclosed wherein one or more of the light absorbing dye is covalently bonded to other structural polymers though ethylene unsaturated groups. The resulting IOLs possess light absorbing properties without significant amounts of free (unbound) azo dye molecules present in the final structural polymer matrix.

21 Claims, No Drawings

FOREIGN PATENT DOCUMENTS

| | | |
|---|---|---|
| JP | 6258604 A | 9/1994 |
| JP | 6262861 A2 | 9/1994 |
| JP | 6324293 A | 11/1994 |
| JP | 7024052 A | 1/1995 |
| JP | 7258166 A2 | 10/1995 |
| JP | 8503997 T | 4/1996 |
| JP | 9187500 A | 7/1997 |
| JP | 10111641 A | 4/1998 |
| JP | 10195324 A | 7/1998 |
| JP | 2003084242 A | 3/2003 |
| JP | 2003144538 A | 5/2003 |
| JP | 2003144638 A | 5/2003 |
| WO | WO8705712 A1 | 9/1987 |
| WO | WO8802871 A1 | 4/1988 |
| WO | WO8907952 A1 | 9/1989 |
| WO | WO9511279 A1 | 4/1995 |
| WO | WO9825173 A1 | 6/1998 |
| WO | WO9825180 A1 | 6/1998 |
| WO | WO9844380 A1 | 10/1998 |

\* cited by examiner

COPOLYMERIZABLE AZO COMPOUNDS AND ARTICLES CONTAINING THEM

CROSS REFERENCE TO RELATED APPLICATIONS

This application is a divisional of U.S. patent application Ser. No. 11/271,344 filed on Nov. 10, 2005, now U.S. Pat. No. 7,326,423 issued on Feb. 5, 2008, which claims the benefit of U.S. provisional patent application No. 60/629,557, filed Nov. 22, 2004, the entire disclosure of which is incorporated herein by reference.

FIELD OF THE INVENTION

This invention relates to polymerizable azo compounds, polymers comprising the residues of such compounds and their use articles, including ophthalmic lenses. In particular, this invention relates to polymerizable yellow light absorbing compounds of the azo class that block ultraviolet light and/or violet-blue light transmission through intraocular lenses.

BACKGROUND OF THE INVENTION

The sun freely emits ultraviolet (UV), visible and infrared (IR) radiation, much of which is absorbed by the atmosphere. Solar radiation that is transmitted through the atmosphere and reaches the earth's surface includes UV-A radiation (320-400 nm), UV-B radiation (290-320 nm), visible light (400-700 nm) and near IR radiation (700-1400 nm). The ocular lens of humans in its normal, healthy state freely transmits near IR and most of the visible spectrum to the retina, but the lens acts to absorb UV radiation to avoid damage to the retina. The ability to absorb near UV and the violet-blue portion of the visible spectrum changes throughout life. In infancy, the human lens will freely transmit near UV and visible light above 300 nm, but with further aging the action of UV radiation from the environment causes the production of yellow colorants, fluorogens, within the lens. Some studies indicate that by age 54 the lens will not transmit light below 400 nm and the transmission of light between 400 and 450 nm is greatly diminished. As the lens ages it continuously develops a yellow color, increasing its capacity to filter out near UV and violet-blue light. Therefore, after cataract removal the natural protection provided by the aged human lens is also removed. Cataracts are typically replaced by an intraocular lens (IOL). If the brain is stimulated by signals caused by the visible light that has not been transmitted for many years, discomfort can result. Development of IOL materials with an absorption similar to aged human lens material would be a welcome improvement to the art.

Although yellow colorants exist, many such colorants are unsuitable for use in artificial lens material due to their tendency to leach out of the IOL after it is inserted in the eye or during solvent extraction associated with lens manufacture. A yellow colorant that is covalently bonded to lens materials would be thus be a desirable improvement in the manufacture of artificial lens materials. Efforts have been made to develop such a lens material. One obstacle of such efforts has been finding a polymerizable colorant that will produce IOLs having an absorption profile that carefully matches that of the aged human lens, especially in the visible spectrum. If the IOL absorbs more than the lens in portions of the visible spectrum, visible acuity can be diminished. If the IOL absorbs less in the visible spectrum, the discomfort discussed above can result. Another obstacle that such efforts have faced has been the need to use a combination of multiple compounds to achieve a careful match with the human lens. Use of multiple compounds can result in a more complicated manufacturing process, along with increased production and materials costs. A polymerizable compound that matches the absorption spectra of the human lens and reduces the need for multiple colorants in an IOL would be a welcome improvement in the art.

More broadly, the development of compounds that provide desired light absorbance and that can be covalently bonded into polymer backbones would have numerous other uses beyond that in artificial lenses. For example, such compounds could be used with a wide array of polymeric applications in which the appropriate absorption spectrum is desired. Thus, what is needed in the art is polymerizable compounds that are more economical and have spectral properties that better suit their target applications.

SUMMARY OF THE INVENTION

The invention solves the problems in the prior art by providing molecules that contain at least one azo group and at least one ethylenically-unsaturated polymerizable group. The azo compounds have the Formula I:

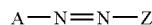

wherein A is an optionally substituted aryl radical and Z is the residue of an azo coupling component selected from the classes of 2-pyrazolin-5-ones, dimedone (5,5-dimethyl-1,3-cyclohexanedione), acetoacetamides, malonamides, barbituric acid and 1,3-propanediones, with the provision that at least one ethylenically-unsaturated polymerizable group must be present on either A or Z with the provision that when Z is 2-pyrazolin-5-one, A is selected from

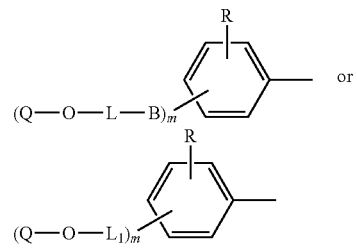

wherein
B is a divalent linking group selected from —CON($R_1$)—, —O—, —S—, and —N($SO_2R_2$)—;
L is selected from $C_2$-$C_8$-alkylene and —[$CH_2CH(R_3)O$]$_n$—$CH_2CH(R_3)$—;
$L_1$ is a $C_1$-$C_8$-alkylene group;
m is selected from 0, 1 and 2;
n is 1, 2, or 3;
R is hydrogen or one to three groups selected from $C_1$-$C_8$-alkyl, $C_1$-$C_8$-alkoxy, halogen, cyano, nitro, thiocyano, trifluoromethyl, —$COR_4$, —$CO_2R_5$, —$SO_2R_2$, —N($R_1$)$COR_4$, —N($R_1$)$SO_2R_2$, arylazo, aryloxy, arylthio, heteroarylthio, —$SO_2N(R_1)R_4$, —CON($R_1$)$R_4$, succinimido, phthalimido, and phthalimidino;
$R_1$ is selected from hydrogen, $C_1$-$C_8$-alkyl, $C_3$-$C_8$-cycloalkyl, $C_3$-$C_8$-alkenyl and aryl;
$R_2$ is selected from $C_1$-$C_8$-alkyl, $C_3$-$C_8$-cycloalkyl and aryl;

$R_3$ is hydrogen or methyl;

$R_4$ is selected from $C_1$-$C_8$-alkyl, $C_3$-$C_8$-cycloalkyl, aryl and hydrogen;

$R_5$ is selected from $C_1$-$C_8$-alkyl, $C_3$-$C_8$-cycloalkyl, aryl and $[CH_2CH(R_3)O]_nCH_2CH(R_3)OR_6$;

$R_6$ is selected from hydrogen, $C_1$-$C_8$-alkyl, aryl, $C_1$-$C_8$-alkanoyloxy and $C_1$-$C_8$-alkoxycarbonyloxy; and Q is an ethylenically-unsaturated polymerizable group;

wherein the molecule comprises at least one ethylenically-unsaturated polymerizable group (Q).

Thus, the invention includes the azo compounds disclosed herein.

The invention further includes compositions comprising the azo compounds of the present invention. In some embodiments, the compositions are polymerizable compositions.

The invention further includes methods of making a polymer comprising polymerizing a group of monomers, prepolymers, chain extenders, or combinations of thereof, one or more of which contains an azo compound of the present invention or a residue of such an azo compound.

The invention further includes polymers that contain the residue of the polymerization of the azo compounds of the present invention.

The invention further includes articles that contain the polymers of the present invention. In some embodiments, the articles are transparent. In some embodiments, the articles are optical objects. In some embodiments, the articles are IOLs.

DETAILED DESCRIPTION OF THE INVENTION

Azo compounds that contain polymerizable, ethylenically-unsaturated moieties are provided. The invention further includes compositions comprising the azo compounds of the present invention. In some embodiments, the compositions are polymerizable compositions. The invention further includes methods of making a polymer comprising polymerizing a group of monomers, prepolymers, chain extenders, or combinations of thereof, one or more of which contains an azo compound of the present invention or a residue of such an azo compound. The invention further includes polymers that contain the residue of the polymerization of the azo compounds of the present invention. The invention further includes articles that contain the polymers of the present invention. In some embodiments, the articles are transparent. In some embodiments, the articles are optical objects. In some embodiments, the articles are IOLs.

Definitions

The following definitions apply to terms as used throughout this application.

The term "$C_1$-$C_8$-alkyl" refers to a straight or branched saturated hydrocarbon radical and said radical optionally substituted with one or two groups selected from hydroxy, halogen, cyano, aryl, $C_3$-$C_8$-cycloalkyl, —$OC_1$-$C_4$-alkyl, —$OCOC_1$-$C_4$-alkyl, —$OCO_2C_1$-$C_4$-alkyl and —$CO_2C_1$-$C_4$-alkyl, wherein the $C_1$-$C_4$-alkyl portion of the groups represents a saturated straight or hydrocarbon radical that contains one to four carbon atoms.

The terms "$C_1$-$C_8$-alkoxy", "$C_1$-$C_8$-alkanoyl", "$C_1$-$C_8$-alkanoyloxy", "$C_1$-$C_8$-alkoxycarbonyloxy" and "$C_1$-$C_8$-alkoxycarbonyl" denote the following radicals: —$OC_1$-$C_8$-alkyl, —$COC_1$-$C_8$-alkyl, —$OCOC_1$-$C_8$-alkyl, —$OCO_2C_1$-$C_8$-alkyl and —$CO_2C_1$-$C_8$-alkyl, respectively, wherein the $C_1$-$C_8$-alkyl radical is as previously defined.

The terms "$C_1$-$C_8$-alkylene" are "$C_2$-$C_8$-alkylene" denote straight or branched divalent hydrocarbon radicals that contain one to eight and two to eight carbons, respectively, with said radicals being optionally substituted with one or two groups selected from hydroxyl, halogen, cyano, aryl, $C_3$-$C_8$-cycloalkyl, —$OC_1$-$C_4$-alkyl, —$OCOC_1$-$C_4$-alkyl, —$CO_2C_1$-$C_4$-alkyl and —OQ, wherein Q is an ethylenically unsaturated polymerizable group.

The term "$C_3$-$C_8$-cycloalkyl" refers to a saturated cyclic hydrocarbon radical containing three to eight carbons with said radical being optionally substituted with $C_1$-$C_4$-alkyl, hydroxy, halogen and $C_1$-$C_4$-alkanoyloxy.

The term "$C_3$-$C_8$-alkenyl" denotes a straight or branched hydrocarbon radical that contains at least one carbon-carbon double bond.

The term "aryl" unless otherwise specified includes phenyl and naphthyl and these groups substituted with one to three groups selected from $C_1$-$C_8$-alkyl, $C_1$-$C_8$-alkoxy, $C_1$-$C_8$-alkoxycarbonyl, halogen, carboxy, cyano, trifluoromethyl, —S—$C_1$-$C_8$-alkyl and —$SO_2C_1$-$C_8$-alkyl.

The term "heteroaryl" includes 5 or 6-membered heterocyclic aryl rings containing one oxygen and/or one sulfur atom, and up to three nitrogen atoms, said heterocyclic aryl rings optionally fused to a phenyl ring. Examples of such systems include thienyl, furyl, pyrrolyl, imidazolyl, pyrazolyl, pyridyl, thiazolyl, isothiazolyl, benzothiazolyl, oxadiazolyl, thiadiazolyl, triazolyl, tetrazolyl, benzoxazolyl, benzimidazolyl and indolyl; these said radicals optionally substituted with one to three groups selected from $C_1$-$C_8$-alkyl, $C_1$-$C_8$-alkoxy, $C_1$-$C_8$-alkoxycarbonyl, —S—$C_1$-$C_8$-alkyl, —$SO_2C_1$-$C_8$-alkyl, trifluoromethyl, cyano, aryl and halogen.

The term "arylene" includes 1,2-, 1,3- 1,4-phenylene and naphthalenediyl and these radicals optionally substituted with one to three groups as previously indicated as substituents on the aryl groups.

The term "halogen" shall mean any atom selected from fluorine, chlorine, bromine and iodine.

The phrase "ethylenically-unsaturated polymerizable group" and/or "free radical initiated polymerizable group" shall mean a moiety having a C=C double bond that is reactive in a free radical polymerization, including but not limited to those having a vinyl group. In some embodiments, the reactive double bond is activated by one of the double-bonded carbons being attached to an aryl group or an electron withdrawing group such as a carbonyl. Although aromatic and heteroaromatic rings are often drawn in this application and elsewhere in a way that depicts the aromatic pi cloud of electrons in such rings as alternating double bonds (for example, benzene is often drawn as a six membered ring containing three alternating double and single bonds) the skilled artisan will understand that such rings do not actually contain double bonds but instead contain an aromatic pi cloud of completely delocalized electrons and, as such, are unreactive to free radical polymerization. Accordingly, none of the terms "reactive C=C double bond," "ethylenically-unsaturated polymerizable group," and "free radical initiated polymerizable group" include aromatic pi clouds of electrons in aromatic or heteroaromatic ring, irrespective of whether such aromatic pi clouds of electrons are representing in any drawing as alternating double bonds.

References herein to groups or moieties having a stated range of carbon atoms, such as "$C_1$-$C_8$-alkyl," shall mean not only the $C_1$ group (methyl) and $C_8$ group (octyl) end points, but also each of the corresponding individual $C_2$, $C_3$, $C_4$, $C_5$, $C_6$, and $C_7$ groups. In addition, it will be understood that each of the individual points within a stated range of carbon atoms may be further combined to describe subranges that are inherently within the stated overall range. For example, the term "$C_3$-$C_8$-cycloalkyl" includes not only the individual cyclic moieties $C_3$ through $C_8$, but also contemplates subranges such as "$C_4$-$C_6$-cycloalkyl."

Azo Compounds

The invention provides azo compounds of Formula I:

$$A-N=N-Z \qquad I$$

wherein A is an optionally substituted aryl radical and Z is the residue of an azo coupling component selected from the classes of 2-pyrazolin-5-ones, dimedone (5,5-dimethyl-1,3-cyclohexanedione), acetoacetamides, malonamides, barbituric acid and 1,3-propanediones, with the provision that at least one ethylenically-unsaturated polymerizable group must be present on either A or Z
with the provision that when Z is 2-pyrazolin-5-one, A is selected from

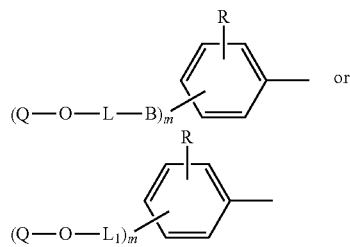

wherein

B is a divalent linking group selected from —CON($R_1$)—, —O—, —S—, and —N($SO_2R_2$)—;

L is selected from $C_2$-$C_8$-alkylene and —[$CH_2CH(R_3)O$]$_n$—$CH_2CH(R_3)$—;

$L_1$ is a $C_1$-$C_8$-alkylene group;

m is selected from 0, 1 and 2;

n is 1, 2, or 3;

R is hydrogen or one to three groups selected from $C_1$-$C_8$-alkyl, $C_1$-$C_8$-alkoxy, halogen, cyano, nitro, thiocyano, trifluoromethyl, —$COR_4$, —$CO_2R_5$, —$SO_2R_2$, —N($R_1$)$COR_4$, —N($R_1$)$SO_2R_2$, arylazo, aryloxy, arylthio, heteroarylthio, —$SO_2N(R_1)R_4$, —$CON(R_1)R_4$, succinimido, phthalimido, and phthalimidino;

$R_1$ is selected from hydrogen, $C_1$-$C_8$-alkyl, $C_3$-$C_8$-cycloalkyl, $C_3$-$C_8$-alkenyl and aryl;

$R_2$ is selected from $C_1$-$C_8$-alkyl, $C_3$-$C_8$-cycloalkyl and aryl;

$R_3$ is hydrogen or methyl;

$R_4$ is selected from $C_1$-$C_8$-alkyl, $C_3$-$C_8$-cycloalkyl, aryl and hydrogen;

$R_5$ is selected from $C_1$-$C_8$-alkyl, $C_3$-$C_8$-cycloalkyl, aryl and [$CH_2CH(R_3)O$]$_n$$CH_2CH(R_3)OR_6$;

$R_6$ is selected from hydrogen, $C_1$-$C_8$-alkyl, aryl, $C_1$-$C_8$-alkanoyloxy and $C_1$-$C_8$-alkoxycarbonyloxy; and Q is an ethylenically-unsaturated polymerizable group;

wherein the molecule comprises at least one ethylenically-unsaturated polymerizable group (Q).

A is any phenyl or napthyl group, optionally substituted at one or more positions. In some embodiments, A has one of the following structures:

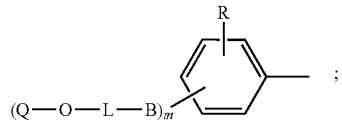

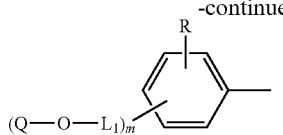

wherein

B is a divalent linking group selected from —CON($R_1$)—, —O—, —S—, and —N($SO_2R_2$)—;

L is selected from $C_2$-$C_8$-alkylene and —[$CH_2CH(R_3)O$]$_n$—$CH_2CH(R_3)$—;

$L_1$ is a $C_1$-$C_8$-alkylene group;

m is selected from 0, 1 and 2, and when m is zero no —B-L-O-Q or -$L_1$-Q groups are present and each represents a hydrogen atom attached to the aromatic ring;

n is 1, 2, or 3;

R represents hydrogen or one to three groups selected from $C_1$-$C_8$-alkyl, $C_1$-$C_8$-alkoxy, halogen, cyano, nitro, thiocyano, trifluoromethyl, —$COR_4$, —$CO_2R_5$, —$SO_2R_2$, —N($R_1$)$COR_4$, —N($R_1$)$SO_2R_2$, arylazo, aryloxy, arylthio, heteroarylthio, —$SO_2N(R_1)R_4$, —$CON(R_1)R_4$, succinimido, phthalimido, and phthalimidino, and the like.

$R_1$ is selected from hydrogen, $C_1$-$C_8$-alkyl, $C_3$-$C_8$-cycloalkyl, $C_3$-$C_8$-alkenyl and aryl;

$R_2$ is selected from $C_1$-$C_8$-alkyl, $C_3$-$C_8$-cycloalkyl and aryl;

$R_3$ is hydrogen or methyl; $R_4$ is selected from $C_1$-$C_8$-alkyl, $C_3$-$C_8$-cycloalkyl, aryl and hydrogen;

$R_5$ is selected from $C_1$-$C_8$-alkyl, $C_3$-$C_8$-cycloalkyl, aryl and [$CH_2CH(R_3)O$]$_n$$CH_2CH(R_3)OR_6$;

$R_6$ is selected from hydrogen, $C_1$-$C_8$-alkyl, aryl, $C_1$-$C_8$-alkanoyl and $C_1$-$C_8$-alkoxycarbonyl;

Q is an ethylenically-unsaturated polymerizable group;

wherein when Z is a coupling component residue not containing at least one Q group then m is one or two.

In some embodiments, the coupling components are as follows:

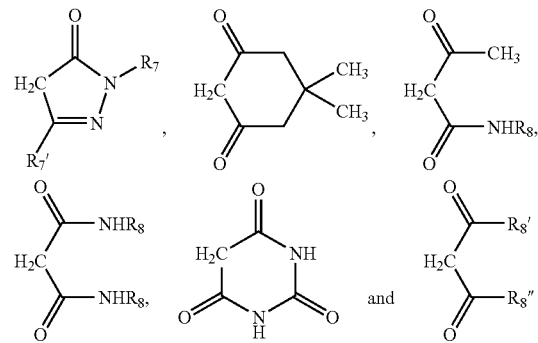

wherein $R_7$ is selected from hydrogen, $C_1$-$C_8$-alkyl, $C_3$-$C_8$-cycloalkyl, aryl, arylene-(B-L-O-Q)$_p$, arylene-($L_1$-O-Q)$_p$ and —$C_2$-$C_8$-alkyleneOQ;

p is one or two and B, L, $L_1$, and Q are as previously defined;

$R_7'$ is selected from $C_1$-$C_8$-alkyl, trifluoromethyl, $C_3$-$C_8$-cycloalkyl, $C_1$-$C_8$-alkoxycarbonyl and aryl;

$R_8$ is hydrogen, $C_1$-$C_8$-alkyl, -$L_1$-O-Q, $C_3$-$C_8$-cycloalkyl, heteroaryl, aryl and aryl substituted with one to three groups selected from $C_1$-$C_8$-alkyl, $C_1$-$C_8$-alkoxy, halogen, —B-L-O-Q and $L_1$-O-Q;

$R_8'$ and $R_8''$ are independently selected from $C_1$-$C_4$-alkyl and aryl.

In some embodiments, the ethylenically-unsaturated polymerizable Q groups include the following organic radicals 1a-9a:

1a  —COC($R_9$)═CH—$R_{10}$,

2a 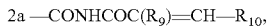 —CONHCOC($R_9$)═CH—$R_{10}$,

3a 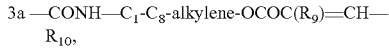 —CONH—$C_1$-$C_8$-alkylene-OCOC($R_9$)═CH—$R_{10}$,

4a 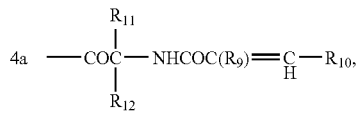

5a 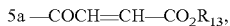 —COCH═CH—$CO_2R_{13}$,

6a 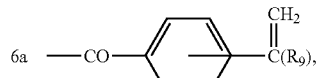

7a 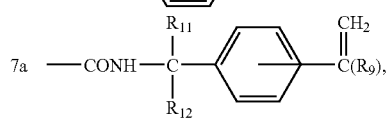

8a 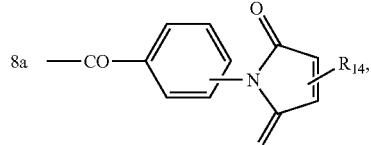

9a 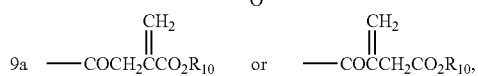 —COCH$_2$ĊCO$_2$R$_{10}$  or  —COĊCH$_2$CO$_2$R$_{10}$, or, where a plurality of azo compounds are involved, a combination of the two on different azo compounds;

wherein:

$R_9$ is hydrogen or $C_1$-$C_8$ alkyl;

$R_{10}$ is: hydrogen; $C_1$-$C_8$ alkyl; phenyl; phenyl substituted with one or more groups selected from $C_1$-$C_8$-alkyl, $C_1$-$C_8$-alkoxy, —N($C_1$-$C_8$-alkyl)$_2$, nitro, cyano, $C_1$-$C_8$-alkoxycarbonyl, $C_1$-$C_8$-alkanoyloxy and halogen; 1- or 2-naphthyl; 1- or 2-naphthyl substituted with $C_1$-$C_8$-alkyl or $C_1$-$C_8$-alkoxy; 2- or 3-thienyl; 2- or 3-thienyl substituted with $C_1$-$C_8$-alkyl or halogen; 2- or 3-furyl; or 2- or 3-furyl substituted with $C_1$-$C_8$-alkyl;

$R_{11}$ and $R_{12}$ are, independently, hydrogen, $C_1$-$C_8$-alkyl, or aryl; or $R_{11}$ and $R_{12}$ may be combined to represent a —(CH$_2$)$_{3-5}$— radical;

$R_{13}$ is hydrogen, $C_1$-$C_8$-alkyl, $C_3$-$C_8$-alkenyl, $C_3$-$C_8$-cycloalkyl or aryl; and $R_{14}$ is hydrogen, $C_1$-$C_8$-alkyl or aryl.

It should be noted that the azo compounds of the present invention are written herein as having the 2-oxyazo Structure i, but that they may exist in the tautomeric azo-enol form ii or the 2-oxyhydrazone form iii, depending upon which conformation is the most thermodynamically favored.

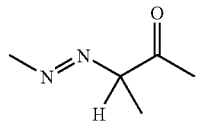

i

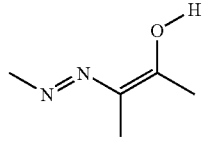

ii

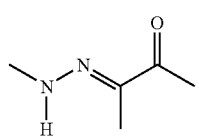

iii

In some embodiments, the ethylenically-unsaturated azo light-absorbing compounds are those of Structure I, wherein A has the structures:

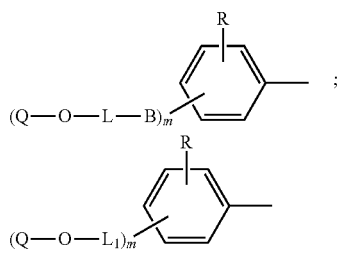

wherein

R is hydrogen, B is —O— or —CONH—;

L is $C_2$-$C_8$-alkylene and —[CH$_2$CH($R_3$)O—]$_n$CH$_2$CH—($R_3$)—;

$L_1$ is $C_1$-$C_8$-alkylene;

$R_3$ is hydrogen or methyl;

m is 1;

n is an integer from 1 to three;

Z is selected from the residue of structures:

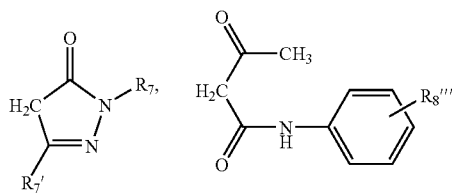

wherein $R_7$ is hydrogen, $C_1$-$C_4$-alkyl and aryl;

$R_7'$ is $C_1$-$C_4$-alkyl and aryl;

$R_8'''$ is hydrogen or one to three groups selected from $C_1$-$C_4$-alkyl, $C_1$-$C_4$-alkoxy and halogen;

Q is selected from the structures:

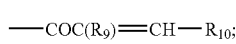 —COC($R_9$)═CH—$R_{10}$;

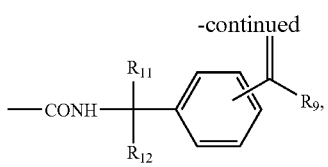

wherein
$R_9$ is hydrogen or methyl;
$R_{10}$ is hydrogen;
$R_{11}$ and $R_{12}$ are methyl.

In some embodiments, the compounds are those having Structure I wherein A has the structure depicted by Formula XIII:

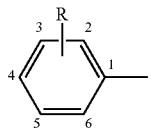

XIII wherein
R is hydrogen or one, two or three groups selected from $C_1$-$C_4$-alkyl, $C_1$-$C_4$-alkoxy, halogen, nitro, cyano and —$CO_2C_1$-$C_8$-alkyl, —$CONHC_1$-$C_8$-alkyl and —$SO_2C_1$-$C_4$-alkyl;
Z is selected from the residue of

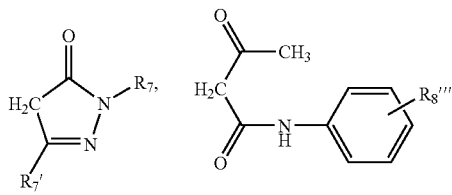

wherein
$R_7$ is selected from

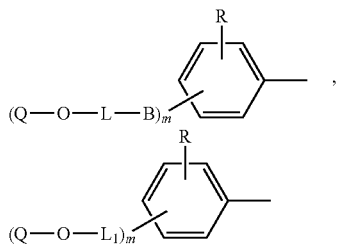

and —$CH_2CH_2$—O-Q;
$R_7'$ is selected from $C_1$-$C_4$-alkyl and aryl;
$R_8'''$ is —B-L-O-Q and -$L_1$-O-Q;
B is —O—;
$R_3$ is hydrogen or methyl;
n is 1, 2, or 3;
m is 1;
L is selected from $C_2$-$C_8$-alkylene and —[$CH_2CH(R_3)O$]$_n$—$CH_2CH(R_3)$—;
$L_1$ is $C_1$-$C_8$-alkylene;

Q is selected from

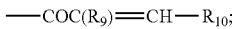

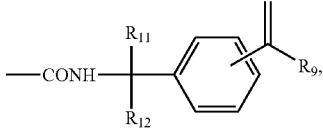

wherein
$R_9$ is hydrogen methyl;
$R_{10}$ is hydrogen; and
$R_{11}$ and $R_{12}$ are methyl.

In one variation of the foregoing embodiment, R represents a 2-$CO_2C_1$-$C_8$-alkyl group or a 2-nitro group in combination with a group in the 4-position selected from $C_1$-$C_4$-alkyl, $C_1$-$C_4$-alkoxy and halogen.

In some embodiments, the compounds of the present invention have a maximum absorption less than 420 nm and have little if any absorption at wavelengths greater than about 450 nm at concentrations that are suitable in the present invention. In some embodiments, the wavelength at which maximum absorption occurs is between about 300 nm and about 420 nm. In some embodiments, there is minimal absorption at 450 nm. In some embodiments, the wavelength of maximum absorption is between about 350 nm and about 390 nm. In some embodiments, the wavelength of maximum absorption is between about 370 nm and about 380 nm. In some embodiments, the wavelength of maximum absorption for UV absorbers is between about 310 nm and about 375 nm. In some embodiments, the wavelength of maximum absorption of the chromophoric unit at wavelength greater than 400 nm is no more than 20 percent of total absorption between about 330 nm and 450 nm.

Methods of Making the Compounds of the Invention

Azo compounds having Structure I prepared by any method are within the present invention. The following procedure provides examples of procedures that can be used to manufacture compounds described by Structure I.

Step 1—Aromatic amines of Structures II and III

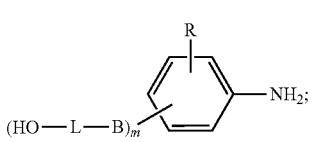

II

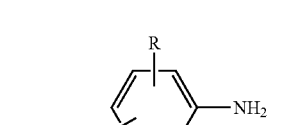

III

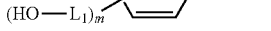

wherein R, B, L, $L_1$ and m are as previously defined are diazotized by conventional procedures and the resulting diazonium salts are coupled with one or more couplers of Structures IV-IX:

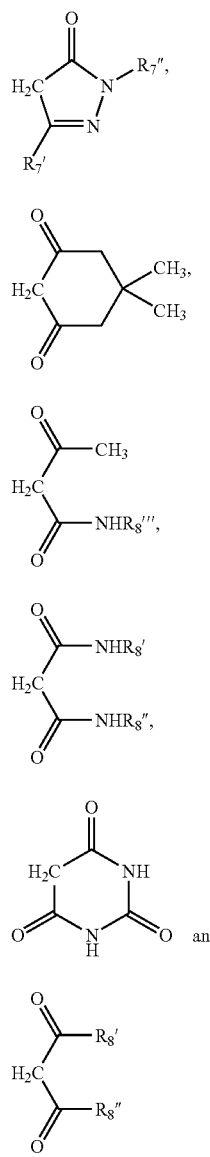

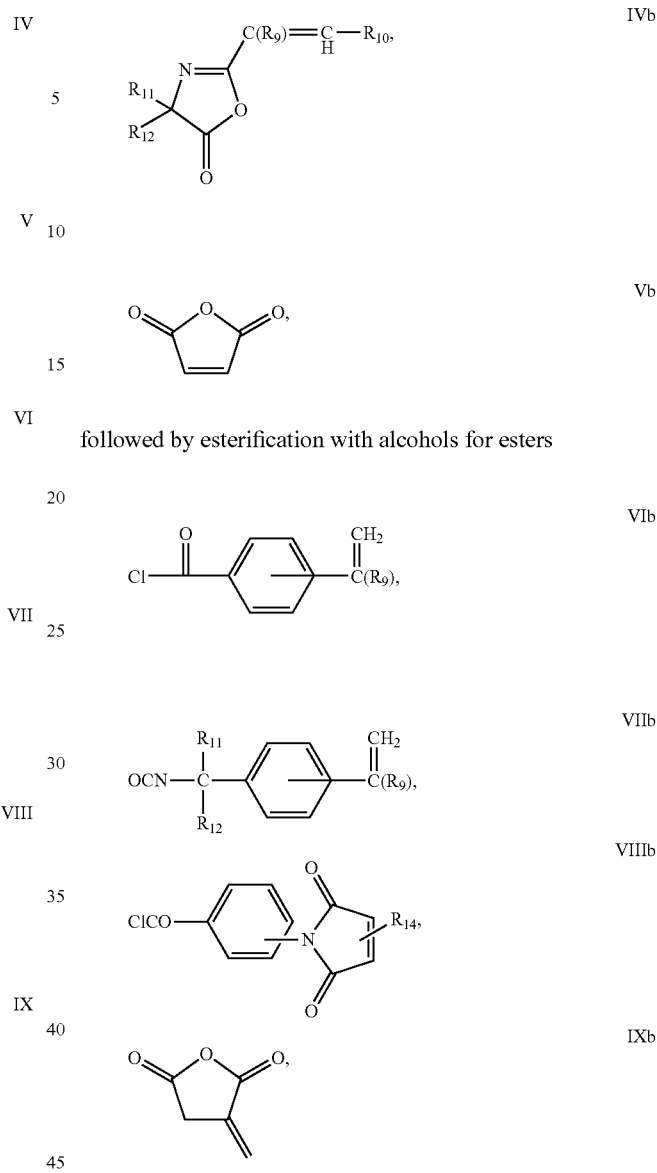

followed by esterification with alcohols for esters wherein $R_9$, $R_{10}$, $R_{11}$, $R_{12}$ and $R_{14}$ are as previously defined.

One synthetic route, however, for the preparation of azo light-absorbing compounds of Structure I wherein B is —CONH— and m is one or two is as follows:

Step Ia—Intermediate aminobenzoic acid esters, particularly the methyl esters of Structure X

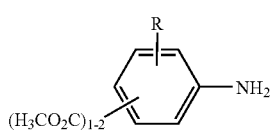

are diazotized to give the corresponding diazonium salts and then coupled with a coupler of Structures IV-IX to give azo compounds containing one or two ester groups having Formula XI wherein $R_7''$ is selected from hydrogen, $C_1$-$C_8$-alkyl, $C_3$-$C_8$-cycloalkyl, aryl, arylene-(B-L-OH)$_p$, arylene-(L$_1$-OH)$_p$ and $CH_2CH_2OH$; $R_8'''$ is hydrogen, $C_1$-$C_8$-alkyl-$L_1$-O—H, $C_3$-$C_8$-cycloalkyl, phenyl and phenyl substituted with one to three groups selected from $C_1$-$C_8$-alkyl, $C_1$-$C_8$-alkoxy, halogen, —B-L-O—H and -$L_1$-O—H; wherein $R_7'$, B, L, $L_1$, p, $R_8'$ and $R_8''$ are as previously defined, with the provision that at least one —B-L-OH or -$L_1$-OH group is present on the azo compound.

Step 2—Azo Compounds from Step 1 that contain one or more —B-L-OH or -$L_1$-OH groups are reacted with one or more acylating agents having Formula Ib-IXb:

ClCOC(R$_9$)=CH—R$_{10}$ OR O[COC(R$_9$)=CH—R$_{10}$]$_2$    Ib

O=C=N—COC(R$_9$)=CH—R$_{10}$,    IIb

O=C=N—C$_1$-C$_8$-alkylene-OCOC(R$_9$)=CH—R$_{10}$,    IIIb

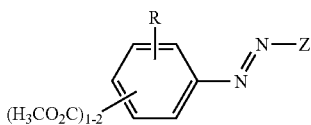

wherein Z and R are as defined previously;

Step IIa—Intermediate esters XI are heated with aminoalkanols of structure H$_2$N-L-OH, where L is as previously defined, to effect an ester-amide interchange reaction and provide the corresponding carboxamide(s) XII:

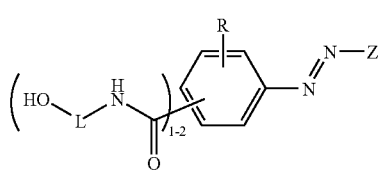

Step IIIa—Azo compounds XII are reacted with acylating agents of Formula Ib-IXb as described in Step II to produce azo compounds of Structure I.

It is understood that different Q groups may exist on A and Z in Structure I. If this structural variation is desired, one Q group may be incorporated into Coupler Z or diazo Component A. These can be converted to azo compounds by diazotizing and coupling with another coupler containing a different Q group to provide compounds with two different Q groups, or a coupler can be chosen that has a hydroxyl group, which provides a compound having a Q group on A and a hydroxyl group on Coupler Z that can be reacted with acylating agents Ib to IXb to introduce another different Q group.

Compositions Comprising the Azo Compounds

Compositions comprising the compounds of the present invention are also provided. The compound can be incorporated in a number of materials in a variety of applications where it is desirable achieve certain desired colors or desired wavelength absorbances.

In some embodiments, the composition is a polymerizable composition containing the azo compounds of the present invention. In some embodiments, the polymerizable composition contains an ultraviolet light absorbing azo compound in combination with a yellow polymerizable compound to obtain the correct shade of yellow while absorbing ultraviolet light in the wavelength range of 300 nm to 400 nm. The amount of compound used will be determined by the application and the spectral properties of the compound. The amount of polymerizable compound can be determined by the thickness of the films (or lens) and by the practitioner. In some embodiments, the amount of yellow polymerizable compound is less that about 4 weight percent based upon the total weight of the resulting polymer. In some embodiments, the amount of yellow polymerizable compound is less that about 4 weight percent based upon the total weight of the resulting polymer. In some embodiments, the amount of yellow polymerizable compound is less that about 2 weight percent based upon the total weight of the resulting polymer. In some embodiments, the amount of yellow polymerizable compound is less than about 1.5 weight percent resulting polymer resulting polymer based upon the total weight of the resulting polymer. In some embodiments, the amount of yellow polymerizable compound is less that about 1 weight percent based upon the total weight of the resulting polymer.

The ultraviolet light absorbing compound will be added in sufficient amount to block the desired amount of ultraviolet light that penetrates the polymer, which is determined by the thickness of the film and the practitioner. In some embodiments, the amount of ultraviolet light absorbing polyermizable compound is less than about 4 weight percent based upon the total weight of the resulting polymer. In some embodiments, the amount of ultraviolet light absorbing polymerizable compound is less than about 2 weight percent based upon the total weight of the resulting polymer. In some embodiments, the amount of ultraviolet light absorbing polyermizable compound is less than about 1.5 weight percent based upon the total weight of the resulting polymer. In some embodiments, the amount of ultraviolet light absorbing polyermizable compound is less than about 1 weight percent based upon the total weight of the resulting polymer. The weight percentages in this paragraph are determined by dividing the weight of compound used in the polymerization by the total weight of the resulting polymer (multiplied by 100 percent).

In some embodiments, the polymerizable composition contains other ultra-violet absorbing compounds in addition to the azo compounds of the present invention. The ultraviolet absorbing material can be any compound which absorbs light having a wavelength shorter than about 400 nm but does not absorb a substantial amount of visible light. In some embodiments, the ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. In some embodiments, an ultraviolet absorbing compound which is copolymerizable with the monomers and is thereby covalently bound to the polymer matrix is used. In this way, the risk of leaching of the ultraviolet absorbing compound out of the lens and into the interior of the eye is reduced. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. In some embodiments, the ultraviolet absorbing compound is 2-(3'-methallyl-2'-hydroxy-5'methyl phenyl)benzotriazole, also known as ortho-methallyl Tinuvin P ("oMTP") is included in the polymerizable composition. Any and all combinations of the other components in the polymerizable composition can be used.

In some embodiments, the polymerizable composition includes a single component polymerizable azo compound that absorbs UV light having a wavelength from 350 nm to 400 and also absorbs the blue-violet light with wavelengths less than about 425 nm or by mixing a co-polymerizable UV absorbing azo compound having a wavelength of maximum absorption of less than about 380 nm and a co-polymerizable azo compound having a wavelength of maximum absorption of between 380 nm and 425 nm to achieve the desired absorption.

In some embodiments, the polymerizable composition contains other monomers that contain ethylenically-unsaturated polymerizable group(s). Any monomers that will polymerize with the compounds of the present invention can be used, including but not limited to hydrogel-forming polymers as well as vinyl-containing monomers such as acrylic, acrylate and/or methacrylate-based monomers. Examples of monomers used in some embodiments include but are not limited to: acrylic acid, methacrylic acid and their anhydrides; crotonic acid; crotonate esters; itaconic acid as well as its anhydride; cyanoacrylic acid as well as its esters; esters of acrylic and methacrylic acids such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, and benzyl acrylate and methacrylate; hydroxyethyl acrylate and methacrylate; diacrylate and dimethacrylate esters of ethylene and propylene glycols, 1,3-butylene glycol, 1,4-butanediol, diethylene and dipropylene glycols, triethylene and tripropylene glycols, 1,6-hexanediol, neopentyl glycol, polyethylene glycol, and polypropylene glycol, ethoxylated bisphenol A, ethoxylated and propoxylated neopentyl glycol; triacrylate and trimethacrylate esters of tris-(2-hydroxyethyl)isocyanurate, trimethylolpropane, ethoxylated and propoxylated trimethylolpropane, pentaerythritol, glycerol, ethoxylated and propoxylated glycerol; tetraacrylate and tetramethacrylate esters of pentaerythritol and ethoxylated and propoxylated pentaerythritol; acrylonitrile; vinyl acetate; vinyl toluene; styrene; N-vinyl pyrrolidinone; alpha-methylstyrene; maleate/fumarate esters; maleic/fumaric acid; 1,6 hexanediol di(meth)acrylate; neopentyl glycol diacrylate; methacrylate; vinyl ethers; divinyl ethers such as diethyleneglycol divinyl ether, 1,6-hexanediol divinyl ether, cyclohexanedimethanol divinyl ether, 1,4-butanediol divinyl ether, triethyleneglycol divinyl ether, trimethylolpropane divinyl ether, and neopentyl glycol divinyl ether, vinyl esters; divinyl esters such as divinyl adipate, divinyl succinate, divinyl glutarate, divinyl 1,4-cyclohexanedicarboxylate, divinyl 1,3-cyclohexanedicarboxylate, divinyl isophthalate, and divinyl terephthalate; N-vinyl pyrrolidone; tetraethylene glycol dimethacrylate; allyl acrylate; allyl methacrylate; trifunctional acrylates; trifunctional methacrylates; tetrafunctional acrylates; tetrafunctional methacrylates; benzyl acrylate; benzyl methacrylate; phenyl acrylate; phenyl methacrylate, phenoxyalkyl acrylates, phenoxyalkyl methacrylates, phenylalkyl acrylates; phenylalkyl methacrylates; carbazole acrylates; carbazole methacrylates; biphenyl acrylates; biphenyl methacrylates; naphthyl acrylates; naphthyl methacrylates; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; hydroxyethylmethacrylate; 2-phenylpropyl acrylate, 2-phenylpropyl methacrylate, N-hexyl acrylate, ethylene glycol dimethacrylate; ethyl methacrylate; N,N-dimethylacrylamide and combinations of one or more of any of the foregoing. One or more additional dye compound monomers are also included in the reaction in some embodiments. By "combinations" it is meant that combinations of two, three, four, or any other number of monomers are within the scope of the present invention. In some embodiments, the compounds are combined with a prepolymer formed from one or more monomers and combined in a chain extension reaction. In some embodiments, the dye compound is formed into a prepolymer, either alone or with one or more other monomers, then chain extended. In some embodiments, all monomers are combined together for a single reaction. All combinations of reactants and polymerization and chain extension steps are within the present invention.

In some embodiments, other monomers include: methyl methacrylate, 2-hydroxyethyl acrylate, 2-hydroxyethyl methacrylate, 3-hydroxypropyl acrylate, 3-hydroxypropyl methacrylate, n-vinyl pyrrolidone, styrene, eugenol (4-hydroxyvinyl benzene), .alpha.-methyl styrene. In addition, for high-refractive index foldable lens applications, suitable monomers include, but am not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate; 2-(4-(1-methylethyl)phenyl ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates, acrylates or combinations thereof. In some embodiments, N-vinyl pyrrolidone, styrene, eugenol and methyl styrene are also used for high-refractive index foldable lens applications. In some embodiments, the monomers are a combination of 2-phenylethyl methacrylate (PEMA) and 2-phenylethyl acrylate (PEA).

In some embodiments, the polymerizable composition includes copolymerizable cross-linking agent, such as a terminally ethylenically-unsaturated compound having more than one ethylenically-unsaturated polymerizable group. Suitable cross-linking agents include but are not limited to: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and 1,4-butanediol diacrylate (BDDA). Suitable crosslinkers also include polymeric crosslinkers, such as, for example, Polyethylene glycol 1000 Diacrylate, Polyethylene glycol 1000 Dimethacrylate, Polyethylene glycol 600 Dimthacrylate, Polybutanediol 2000 Dimethacrylate, Polypropylene glycol 1000 Diacrylate, Polypropylene glycol 1000 Dimethacrylate, Polytetramethylene glycol 2000 Dimethacrylate, and Polytetramethylene glycol 2000 Diacrylate.

In some embodiments, the polymerizable composition includes one or more thermal free radical initiators. Examples of such initiators include, but are not limited to peroxides, such as benzoyl peroxide, peroxycarbonates, such as bis-(4-tert-butylcyclohexyl) peroxydicarbonate (PERK), azonitriles, such as azo-bis-(isobutyronitrile) (AIBN), and the like.

The foregoing are simply examples of components that may be in polymerizable compositions and other compositions of the present invention. Every effective combination of two or more of the foregoing components is within the present invention. Furthermore, the foregoing examples are not intended to be limited, and any desirable or acceptable component can be included in the compositions of the present invention.

Polymers and Polymerization Processes

The invention further provides compositions comprising the polymers of the present invention. Such compositions may contain any other suitable component. In some embodiments, the composition includes both one or more polymer of the present invention and one or more azo compounds of the present invention. In some embodiments, the azo compounds are polymerized essentially alone to form polymers formed form monomeric azo compounds. In some embodiments, the azo compounds are polymerized along with other monomers.

The polymers contain the residues of free radical polymerization reaction of azo compounds and other monomers. Any method of free radical polymerization reaction is within the present invention. In addition, the product resulting from polymerization of any of the polymerizable compositions of the present invention, including each combination disclosed above, are also included. Any polymer containing a residue of the free radical polymerization of an azo compound of the present invention is within the present invention.

The polymerization methods of this invention include all effective polymerization methods. A mixture of ultraviolet light absorbing compounds and/or violet-blue light blocking (yellow) compounds in the desired proportions together with a conventional thermal free-radical initiator. The mixture can then be introduced into a mold of suitable shape to form the lens, and the polymerization may be carried out by gentle heating to activate the initiator. Examples of thermal free radical initiators include, but are not limited to peroxides, such as benzoyl peroxide, peroxycarbonates, such as bis-(4-tert-butylcyclohexyl) peroxydicarbonate (PERK), azonitriles, such as azo-bis-(isobutyronitrile) (AIBN), and the like.

In some embodiments, the monomers are photopolymerized by using a mold which is transparent to actinic radiation of a wavelength capable of initiating polymerization of these monomers. Conventional photoinitiator compounds, e.g., a benzophenone-type photoinitiator, are optionally introduced to facilitate the polymerization. Photosensitizers can be introduced as well to permit the use of longer wavelengths. In some embodiments of polymers intended for long residence within the eye, the number of ingredients in the polymer is minimized to decrease the risk of having materials leach from the lens into the interior of the eye.

In some embodiments, these monomers are cured directly in a polypropylene mold so that a finished optic is produced. The time and temperature for curing vary with the particular lens-forming material chosen. The optic may be combined in a number of known ways with a variety of known haptics to produce an IOL.

Articles

The invention also provides articles that contain the azo compounds of the present invention, the polymers of the present invention, the compositions of the present invention, or a combination thereof of the present invention. In some embodiments, an entire article is made of one or more azo compounds, polymers, or compositions of the present invention. In some embodiments, an entire article is made of a mixture, solution, or other combination that includes one or more azo compound, polymer, or compositions of the present invention. In some embodiments, a component of the article is made is made of one or more azo compounds, polymers, or compositions of the present invention. In some embodiments, a component of the article is made is made of a mixture, solution, or other combination that includes one or more azo compound, polymer, or compositions of the present invention. Articles that include more than one azo compound, polymer, composition, or combination thereof of are also within the present invention.

In some embodiments, the article is or includes a component that is transparent or otherwise permeable to certain wavelengths of visible light. In some embodiments, the article is an optic lens such as lenses useful in windows, contact lenses, telescopes, eyeglasses or sunglasses. In some embodiments, the article is an ocular lens used as an IOL.

In some embodiments, the articles include coatings that contain azo compounds of the present invention. Such coatings are produced by any means, including but not limited to casting, spin casting, dipping, immersion, or spraying.

In some embodiments, the azo compounds or polymers are applied in a liquid carrier such as a solvent. After coating, the carrier is removed (for example, by evaporation of the solvent) leaving the compound or polymer on the coated substrate. In some embodiments, the coating is present as a yellow film and/or a UV absorbing film onto a substrate.

Methods of making the articles of the present invention are also within the present invention. In some embodiments, one or more of the polymerizable azo compounds of this invention are dissolved into a suitable monomer formula, cast onto a substrate (e.g. a transparent material) and cured by a suitable free-radical initiation procedure, such as exposure to heat or UV radiation.

In some embodiments, the azo compounds of this invention are dissolved into a suitable solvent or monomer formula, followed by immersion of an article or material into the solution containing the azo compound. The solution enters the polymer (for example, by absorption) then the polymer is dried. The result is incorporation into the matrix of the polymer. The polymerizable azo compounds are then cured, for example by heat, radiation or other means suitable to bond the azo compound into the polymer.

In some embodiments, the polymerizable azo compounds may undergo addition reaction to silicone having hydrosilyl groups, the addition reaction using a catalyst such as platinum can provide a silicone compounds having a very little fear of elution of the dye directly bound to the silicone. Examples of the above silicone compounds having hydrosilyl groups are dimethylsiloxane-methylhydrosiloxane copolymer, diphenylsiloxane-phenylhydrosiloxane copolymer, polyethylhydrosiloxane, methylhydrosiloxane-phenylmethylsiloxane copolymer, methylhydrosiloxane-octylmethylsiloxane copolymer, methyl silicone resin containing hydrosilyl groups, polyphenyl (dimethylhydrosiloxy) siloxane and the like, but these are not limited. Catalysts using in the addition reaction of the polymerizable azo compounds to silicone compounds are desirably platinum compounds such as hydrogen chloroplatinate, platinum-divinyltetramethyldisiloxane, and platinum-tetramethyltetravinylcyclosiloxane. Further, a silicone bound to the polymerizable azo compounds obtained by the above method provides a silicone elastomer chemically bound to the polymerizable azo compounds by crosslinking with a silicone having vinyl groups. Further, a silicone bound to the above polymerizable azo compounds provides a silicone elastomer chemically bound to the polymerizable azo compounds by crosslinking with a mixture of silicone having vinyl groups and silica. To form the above elastomer, catalysts such as platinum compounds such as hydrogen chloroplatinate, a platinum-divinyltetramethyl-disiloxane complex, a platinum-tetramethyltetravinylcyclotetrasiloxane complex and a platinum-alumina supporting catalyst can be used, and such catalysts provide a smooth crosslinking reaction. The polymerizable azo compounds of the present invention can be chemically bound to silicone having hydrosylil groups and then crosslinked with silicone having vinyl groups. The other method is that the polymerizable azo compounds of the present invention is mixed with silicone having hydrosilyl groups or silicone having vinyl groups, and the mixture is mixed with silicone having hydrosilyl groups and silicone having vinyl groups, and then the mixture is cross-linked at the same time the polymerizable azo compounds is reacted to the hydrosilyl groups. At the mixing with silicone described above, it is preferable to homogeneously disperse the polymerizable azo compounds by using an appropriate solvent. As such solvents, acetone, ethanol, methanol, tetrahydrofuran, dichloromethane can be exemplified. To the solvent, the polymerizable azo compounds is dissolved and mixed with silicone. Then, the solvent is distilled away with an evaporator, and the polymerizable azo compounds can be uniformly dispersed in silicone.

This invention can be further illustrated by the following examples, although it will be understood that these examples are included merely for purposes of illustration and are not intended to limit the scope of the invention.

EXAMPLES

Examples 1a through 9c describe actual procedures that were performed in preparing some of the compounds of the present invention and their precursors. Each of Examples 1a through 9c includes a drawing to show the product. Examples 10 through 84 are prophetic examples of some of the azo compounds that are within the present invention.

Examples 85 through 87 describe examples of some of the procedures for preparing a polymer and polymerizing azo compounds.

Example 1a

To a solution prepared by adding conc. HCl (36 mL) to water (100 mL) is added with stirring 4-aminophenethyl alcohol (16.44 g, 0.12 mol, Aldrich). The solution is cooled and a solution of sodium nitrite (8.64 g, 0.15 mol) dissolved in water (32 mL) is added below 3° C. and stirring continued for 2 hours at 0-3° C. A coupling solution of 3-methyl-1-phenyl-2-pyrazolin-5-one (20.9 g, 0.12 mol, Aldrich) dissolved in water (800 mL) containing 50% aqueous sodium hydroxide (26.5 g) is prepared. The solution is stirred and cooled in an ice water bath and portions of ice added for internal cooling. The diazonium salt solution, as prepared above, is added dropwise with stirring and cooling continued to maintain temperature at about 3-5° C. Stirring is continued at about 5° C. for about 1.0 hour and the solid yellow product is collected by vacuum filtration, washed with water and then dried in air. The yield is 37.8 g (97.9% of one theoretical) of product which had the following structure and assayed 96.2% by liquid chromatography/mass spectral analysis (LC/MS). The azo compound had an absorption maximum ($\lambda_{max}$) at 403 nm in N,N-dimethylformamide (DMF) in the UV-visible light absorption spectrum.

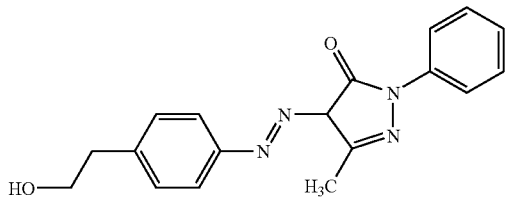

Example 1b

A portion of the product from Example 1a (35.4 g, 0.11 mol), 4-dimethylaminopyridine (DMAP), (0.7 g, 6 mmol), hydroquinone (0.35 g) and triethylamine (14.5 g, 0.375 mol) are added to dry acetone (275 mL) with stirring. Methacrylic anhydride (21.7 g, 0.14 mol, Aldrich) is added and the reaction mixture stirred and heated at reflux. After 1.5 hour the progress of the reaction is checked by thin-layer chromatography (TLC). Some hydroxyl containing starting material is still present. Additional methacrylic anhydride (5 mL) is added and heating and stirring continued at reflux temperature for 1.0 hour.

Reaction is complete by TLC. The reaction mixture is allowed to cool to room temperature and a yellow solid product results. Cold methanol (100 mL) is added to further precipitate the product and the mixture is stirred and cooled to about 15° C. The product is collected, washed with cold methanol and dried in air (yield—36.6 g, 78.3% of the theoretical yield). The precipitate has the following structure by LC/MS and the purity is estimated to be about 96%. The compound exhibits a wavelength of maximum absorption ($\lambda_{max}$) at 408 nm and a molar absorptivity ($\epsilon$) of $2.21 \times 10^4$ as determined by UV-visible light spectroscopy in DMF.

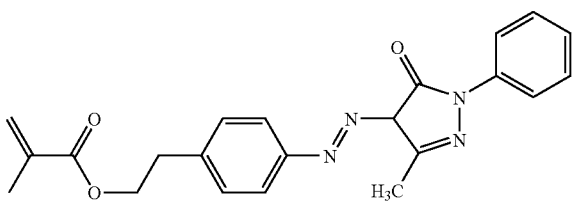

Example 2a

Acetic acid (180 mL) is added to water (120 mL) with stirring and the solution cooled in an ice/water bath while methyl anthranilate (15.1 g, 0.10 mol) is added below 25° C. The solution is further cooled and 40% nitrosylsulfuric acid (32.0 g, 0.1 mol) added dropwise below 5° C. Stirring is continued for 2.0 hours at 0-5° C. and half of the diazonium solution is added to a cold solution of 3-methyl-1-phenyl-2-pyrazolin-5-one (17.4 g, 0.10 mol, Aldrich) dissolved in cold water (500 mL) to which 50% NaOH (40.0 g) has been added. Ice is added during the addition of the diazonium salt to keep the temperature at about 0-2° C. A thick slurry of yellow solid results and cold water (400 mL) is added to facilitate stirring. An additional quantity (50 g) of 50% NaOH solution is added and then the remaining half of the diazonium salt solution is added gradually still keeping the temperature at 0-5° C. At this point, the mixture is neutral to Congo Red test paper (pH of about 4). The mixture is stirred in the cold for about 45 minutes and then the yellow solid is collected by filtration, washed with cold water, then with warm water, and dried in air (yield 32.4 g., 96% of the theoretical yield). By LC/MS analysis, the product has the following structure:

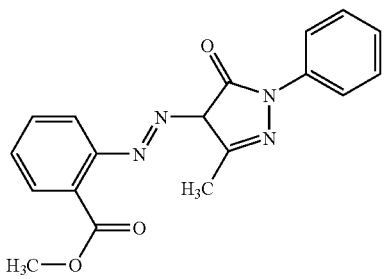

with an assay of 98.3% by area percent.

Example 2b

A mixture of a portion of the ester compound of Example 2a (16.8 g, 0.050 mol), 1-amino-2-propanol (75 mL) and n-propanol (125 mL) is heated with stirring to about 105° C. After stirring for about 15-20 minutes at 105° C., a yellow solid begins to precipitate. The reaction mixture is heated for approximately another hour and then allowed to cool. To the thick slurry of yellow amide product is added water (150 mL) dropwise with stirring and then the entire slurry is poured into cold water (400 mL) with stirring. The yellow product is collected by filtration, washed with cold water followed by a little cold methanol, and then dried in air to yield 13.5 g of fluffy yellow solid (71% of the theoretical yield). LC/MS analysis shows the product to have the following structure

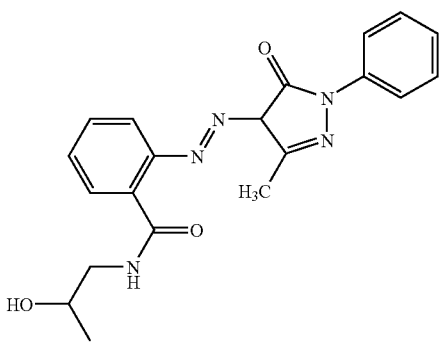

and to have a purity of 98.8% by area percent.

Example 2c

A portion of the hydroxy-containing compound from Example 2b (10.0 g, 26.4 mmols) and acetone (250 mL) are mixed and stirred. To this mixture are added DMAP (0.19 g), hydroquinone (0.1 g), triethylamine (4.59 mL, 33.0 mmols) and methacrylic anhydride (4.91 mL, 33.0 mmols) and the reaction mixture is heated at reflux for about 5.0 hours. By TLC only a small amount of the hydroxyl compound has been esterified. DMF (25 mL) is added to increase solubility of the starting hydroxyl compound and heating and stirring at about 55-60° C. are continued for about 20 hours. Most of the hydroxyl compound appears to be esterified by TLC analysis. Heating is discontinued and the cooled slurry is poured into methanol (100 mL) while stirring. The yellow solid is collected by filtration and washed with cold acetone (25 mL). FD/MS indicates that most of this solid is the starting yellow hydroxyl compound. The filtrate is allowed to stand in a closed flask over the weekend. Methanol (100 mL) is added to the filtrate and the yellow precipitate is collected by filtration, washed with a small amount of methanol and dried in air to yield 6.73 g (57% of the theoretical yield). LC/MS indicates the yellow solid to be mostly the esterified product:

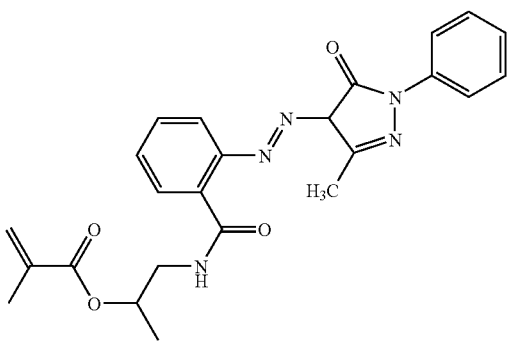

and to have a purity of about 85% by area percent. The azo compound has an absorption maximum ($\lambda_{max}$) at about 433 nm in the UV-visible absorption spectrum in DMF solvent.

Example 3

A portion of the hydroxyl compound from Example 1a, 4-[4'-(2'-hydroxyethyl)phenylazo]-3-methyl-2-pyrazolin-5-one (2.42 g, 7.5 mmol), 3-isopropenyl-2,2-dimethylbenzyl-isocyanate, Aldrich, assay 95% (1.60 g; 1.52 g, 7.6 mmol—based upon 100% assay) and toluene (35 mL) are mixed and heated at 90° C. with stirring. After 0.5 hour, thin-layer chromatography (TLC) (1:1 tetrahydrofuran:cyclohexane) indicates considerable quantity of starting hydroxyl compound present.

Twenty drops of dibutyltin dilaurate catalyst are added and heating and stirring continued for another 0.5 hour. TLC shows essentially complete esterification. The reaction mixture is heated for an additional 20 minutes and then allowed to cool. After being drowned into cold heptane (200 mL), the solid yellow product is collected by filtration, washed with cold heptane and dried in air to yield 3.23 g (82% of the theoretical yield). Field desorption mass spectrometry (FD/MS) indicates that the compound has the following structure:

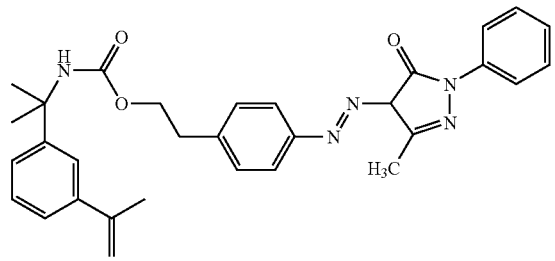

Examples 4a-4d

A solution is prepared by the addition of 4-aminophenethyl alcohol (11.0 g, 0.08 mol) to water (65 mL) to which conc. HCl (24 mL) has been added with stirring. The solution is cooled in an ice bath and a solution of sodium nitrite (5.76 g) dissolved in water (22 mL) is added dropwise at less than 3° C. with stirring. After being stirred for 2.0 hours at 0-5° C., a 0.02 mol aliquot of diazonium salt is added to a solution of each of the following couplers (Eastman Chemical Company) which had been dissolved in water (100 mL) that contains 50% NaOH (6.5 g) with crushed ice added for internal cooling:

Example 4a—Acetoacet-2-toluidide

Example 4b—Acetoacet-2,4-xylidide

Example 4c—Acetoacet-2-chloroanilide

Example 4d—Acetoacet-2-anisidide

The pH is adjusted by adding a little acetic acid to neutralize the excess NaOH and to further precipitate the azo compounds. The coupling mixtures are allowed to stand at about 0-5° C. for 1 hour with occasional stirring and then drowned into about 400 mL of water with stirring. The solid 4-(2-hydroxyethyl)phenylazoacetoacetarylide compounds were collected by filtration, washed with water and dried in air (yields: Example 4a-5.0 g; Example 4b-4.8 g; Example 4c-7.1 g; Example 4d-6.2 g).

Example 5

A portion of the compound of Example 4a (3.39 g, 0.01 mol), 4-(dimethylamino)pyridine (0.06 g) and hydroquinone (0.03 g) are added with stirring to acetone (25 mL). Triethylamine (2.0 mL) is added followed by methacrylic anhydride (2.2 mL) and the reaction mixture is heated and stirred at about 50° C. for about 30 minutes. TLC shows essentially complete reaction. After being cooled in an ice bath the reaction mixture is treated with a cold solution of methanol/water, 2:1 by volume, followed by an additional 10 mL of cold water, all dropwise with stirring. The solid yellow product is collected by filtration, washed with a little 2:1 methanol:water by volume and dried in air. The yield of product is 3.56 g (87.5% of the theoretical yield), which has the following structure as evidenced by FD/MS.

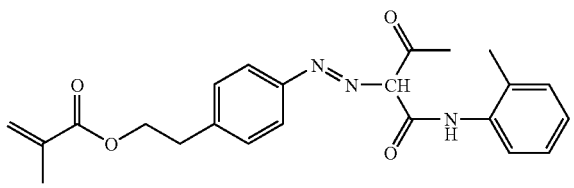

The compound exhibits a wavelength of maximum of absorbance (λ max) at 380.8 nm and a molar absorptivity (ε) of 24,4000 as determined by UV-visible light spectroscopy in DMF solvent.

Example 6

A portion of the azo compound from Example 4b (2.65 g, 0.0075 mol), 4-(dimethylamino)pyridine (0.04 g), and hydroquinone (0.03 g) are added to acetone (25 mL) with stirring. Triethylamine (2.0 mL) is added, followed by methacrylic anhydride (2.0 mL). The reaction mixture is heated at reflux temperature for 30 minutes whereupon TLC (1:1 tetrahydrofuran:cyclohexane) indicates complete esterification. The reaction mixture is cooled in an ice bath and 25 mL of a cold solution of 2:1 methanol:water by volume is added dropwise with stirring. The yellow product is collected by filtration and washed with a little cold 2:1 methanol:water solution and then dried in air. The yield of the product is 2.46 g (77.8% of the theoretical yield), which has the following structure as evidenced by FD/MS:

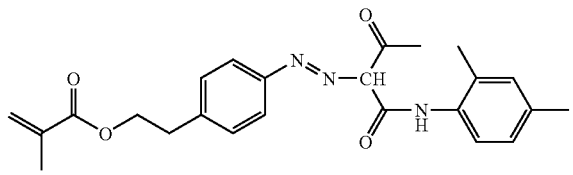

The compound exhibits a wavelength of maximum absorption ($\lambda_{max}$) at 381.1 nm and a molar absorptivity (ε) of 26,600 as determined by UV-visible light-spectroscopy in DMF solvent.

Example 7

A portion of the compound of Example 4c (2.70 g, 0.0075 mol), 4-(dimethylamino)pyridine (0.04 g), hydroquinone (0.03 g), triethylamine (2.0 mL) methacrylic anhydride (2.0 mL) are mixed and reacted in acetone (30 mL) and the resulting esterified product isolated as described in Example 6. The yield of product is 1.83 g (57.0% of the theoretical yield), which has the following structure by FD/MS.

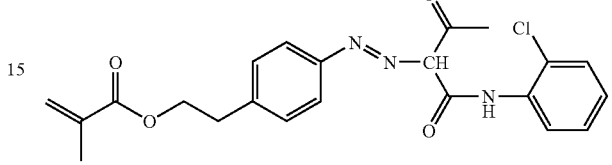

The compound exhibits a wavelength of maximum absorption ($\lambda_{max}$) at 380 nm and a molar absorptivity (ε) of 45,000 as determined by UV-visible spectroscopy in DMF.

Example 8

A portion of the compound of Example 4d (2.66 g, 0.0075 mol), 4-(dimethylamino)pyridine (0.04 g), hydroquinone (0.03 g), triethylamine (2.0 mL) and methacrylic anhydride (2.0 mL) are added to acetone (30 mL) with stirring, reacted, and the resulting product isolated as described in Example 6. The yield of product is 2.28 g (71.9% of the theoretical yield), which has the following structure as evidenced by FD/MS:

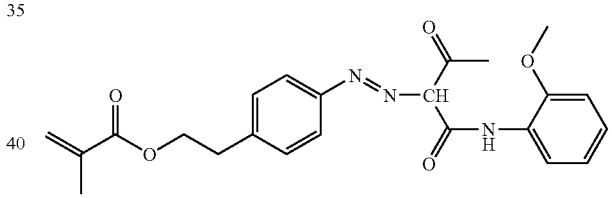

The compound exhibits a wavelength of maximum absorption ($\lambda_{max}$) at 384 nm and a molar absorptivity (ε) of 25,900 as determined by UV-visible light spectroscopy in DMF as solvent.

Example 9a

Methyl 4-aminobenzoate (15.1 g, 0.10 mol) is added portionwise with stirring to water (100 mL) that contains conc. HCl (30 mL). The temperature is increased to about 40° C. to facilitate dissolution of the solid. The solution is cooled to about 0° C. and a solution of sodium nitrite (7.2 g) that has been dissolved in water (20 mL) is added dropwise with stirring and cooling about 0° C. After being stirred at 0-5° C. for about 1.0 hour, the diazotization reaction solution is added dropwise to a solution of 1-phenyl-3-methyl-5-pyrazolone (17.4 g, 0.1.0 mol) dissolved in water (450 mL) that contains 50% NaOH 50.0 g) and crushed ice for cooling, to keep the temperature at about 2-3° C. The coupling mixture is stirred at less than 5° C. for about 1 hour and then allowed to warm to about 18° C. The yellow product is collected by filtration, washed with water and dried in air (yield—33.6 g, 99.6% of the theoretical yield). FD/MS supports the following structure:

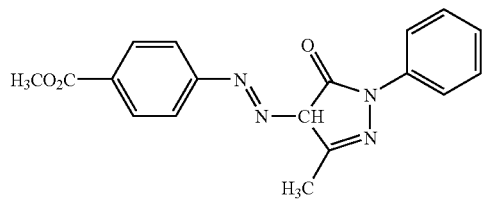

Example 9b

Ethanolamine (20.0 g) is heated to about 90° C. with stirring on a steam bath. A portion of (13.4 g, 0.040 mol) the azo compound from Example 9a is added portionwise with stirring. After being heated at about 95-100° C. for 2.0 hours, TLC shows some of starting ester compound. Additional ethanolamine (5.0 mL) is added and the reaction mixture is heated at 95-100° C. for another hour, whereupon the ester-amide interchange reaction appears to be complete by TLC. The solution is poured gradually into water (70 mL) that contains acetic acid (15 mL). When the drowning mixture becomes very thick additional water (~200 mL) is added as needed to facilitate stirring. The mixture is allowed to cool to about room temperature and the yellow product is collected by filtration, washed with water and dried at 60° C. The yield is 13.9 g (95.1% of the theoretical yield) of product having the following structure by as evidenced by FD/MS:

Example 9c

A mixture of the hydroxyl containing azo compound of Example 9b (1.46 g, 0.0040 mol), 3-isopropenyl-α,α-dimethylbenzylisocyantate (1.0 g), dibutyltin dilaurate (2 drops) and toluene (25.0 mL) is heated at 90° C. with stirring for about 30 min. Some undissolved starting material still remains. Additional toluene (10.0 mL) and 3-isopropenyl-α,α-dimethylbenzylisocyanate (10 drops) are added and the temperature is increased to 100° C. Solution occurs and stirring and heating are continued for about 45 minutes (TLC 1:1 tetrahydrofuran:cyclohexane). The reaction solution is allowed to cool to about room temperature and then drowned into chilled heptane (150 mL) with good stirring. The solid azo product is collected by filtration, washed with heptane and dried in air. The yield 2.0 g (92.0% of the theoretical yield) of yellow azo product that has the following structure as evidenced by FD/MS.

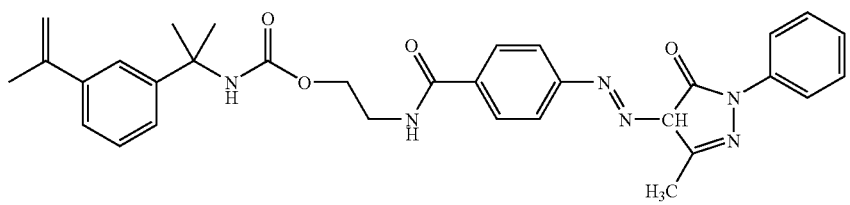

TABLE I

Ethylenically-unsaturated Yellow Azo Compounds

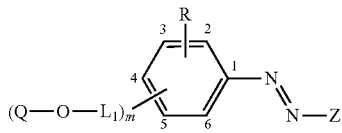

| Example No. | Q | L1 | m | R | Z |
|---|---|---|---|---|---|
| 10 | —COC(CH$_3$)=CH$_2$ | 2-CH$_2$—CH$_2$— | 1 | H | 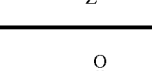 |

TABLE I-continued

Ethylenically-unsaturated Yellow Azo Compounds $$(Q-O-L_1)_m \text{-C}_6H_3(R)\text{-N=N-Z}$$

| Example No. | Q | L1 | m | R | Z |
|---|---|---|---|---|---|
| 11 | —COC(CH$_3$)=CH$_2$ | 3-CH$_2$— | 1 | H | 4-methyl-2-phenyl-5-C$_6$H$_5$-pyrazol-3(2H)-one |
| 12 | —CONHC(CH$_3$)$_2$-1,3-C$_6$H$_4$—C(CH$_3$)=CH$_2$ | 3-CH(CH$_3$)— | 1 | H | 4-methyl-2-phenyl-5-CF$_3$-pyrazol-3(2H)-one |
| 13 | —COC(CH$_3$)=CH$_2$ | 3,5-di-CH$_2$— | 2 | 4-CH$_3$ | 4-methyl-2-(C$_6$H$_4$-4-OCH$_3$)-5-CH$_3$-pyrazol-3(2H)-one |
| 14 | —COCH=CH$_2$ | 3,5-di-CH$_2$— | 2 | 4-C$_2$H$_5$ | 4-methyl-2-(CH$_2$CH$_2$OCOCH=CH$_2$)-5-CH$_3$-pyrazol-3(2H)-one |
| 15 | Q—O—L$_1$— = hydrogen | Q—O—L$_1$— = hydrogen | 0 | 2-CO$_2$CH$_3$ | 4-methyl-2-(CH$_2$CH$_2$OCOC(CH$_3$)=CH$_2$)-5-CH$_3$-pyrazol-3(2H)-one |
| 16 | Q—O—L$_1$— = hydrogen | Q—O—L$_1$— = hydrogen | 0 | 2-NO$_2$-4-CH$_3$ | 4-methyl-2-(C$_6$H$_4$-4-CH$_2$CH$_2$OCOC(CH$_3$)=CH$_2$)-5-CH$_3$-pyrazol-3(2H)-one |
| 17 | Q—O—L$_1$— = hydrogen | Q—O—L$_1$— = hydrogen | 0 | 2-NO$_2$-4-Cl | CH$_3$COCH(CH$_3$)CONHCH$_2$CH$_2$OCOC(CH$_3$)=CH$_2$ |
| 18 | Q—O—L$_1$— = hydrogen | Q—O—L$_1$— = hydrogen | 0 | 2-NO$_2$-4-OCH$_3$ | CH$_3$COCH(CH$_3$)CONH-(3-C$_6$H$_4$)-CH$_2$OCOC(CH$_3$)=CH$_2$ |

TABLE I-continued

Ethylenically-unsaturated Yellow Azo Compounds

General structure: phenyl ring with positions 1-6, where position 1 bears —N=N—Z, position 2 bears R, and position 4/5 bears (Q—O—L1)$_m$

| Example No. | Q | L1 | m | R | Z |
|---|---|---|---|---|---|
| 19 | —CONHC(CH$_3$)$_2$-1,3-C$_6$H$_4$—C(CH$_3$)=CH$_2$ | 4-CH$_2$CH$_2$— | 1 | H | —CH(COCH$_3$)CONHC$_6$H$_5$ |
| 20 | —CONHCH$_2$CH$_2$OCOC(CH$_3$)=CH$_2$ | 3-CH$_2$— | 1 | H | 2-methyl-3-oxo-N-(4-chloro-2,5-dimethoxyphenyl)butanamide |
| 21 | —COC(CH$_3$)$_2$NHCOC(CH$_3$)=CH$_2$ | 3-CH(C$_6$H$_5$) | 1 | H | 2-methyl-3-oxo-N-(4-ethoxyphenyl)butanamide |
| 22 | —COCH$_2$C(CO$_2$CH$_3$)=CH$_2$ | 2-CH$_2$CH$_2$— | 1 | H | 2-methyl-3-oxo-N-(5-chloro-2-methoxyphenyl)butanamide |
| 23 | 1-(4-acetylphenyl)-1H-pyrrole-2,5-dione | 3,5 di-CH$_2$— | 2 | 4-CH$_3$ | 2-methyl-3-oxo-N-(4-chlorophenyl)butanamide |
| 24 | —COCH=CH—CH$_3$ | 3,5 di-CH$_2$— | 2 | 4-CH$_3$ | —CH(COCH$_3$)CONH$_2$ |
| 25 | —COCH=CH—C$_6$H$_5$ | 3,5 di-CH$_2$— | 2 | 4-CH$_3$ | —CH(COCH$_3$)CONC$_6$H$_{11}$ |
| 26 | (E)-4-(furan-2-yl)but-3-en-2-one | 4-CH$_2$CH$_2$— | 1 | H | —CH(CONHC$_6$H$_5$)$_2$ |
| 27 | (E)-4-(thiophen-2-yl)but-3-en-2-one | 4-CH$_2$CH$_2$— | 1 | H | 2-methyl-3-oxo-N-(2-ethylhexyl)butanamide |
| 28 | —CONHCOC(CH$_3$)=CH$_2$ | 4-CH$_2$CH$_2$— | 1 | H | —CH(COCH$_3$)$_2$ |
| 29 | 1-(4-vinylphenyl)ethan-1-one | 4-CH$_2$CH$_2$— | 1 | H | —CH(COCH$_3$)COC$_6$H$_5$ |
| 30 | —COC(CH$_3$)=CH$_2$ | 4-CH$_2$CH$_2$— | 1 | H | —CH(COC$_6$H$_5$)$_2$ |
| 31 | —COC(CH$_3$)=CH$_2$ | 3-CH$_2$ | 1 | H | 2,5,5-trimethylcyclohexane-1,3-dione-substituted |

TABLE I-continued

Ethylenically-unsaturated Yellow Azo Compounds

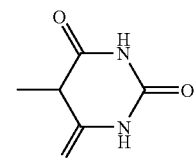

| Example No. | Q | L1 | m | R | Z |
|---|---|---|---|---|---|
| 32 | —COC(CH₃)=CH₂ | 4-CH₂CH₂— | 1 | H | 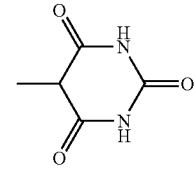 |
| 33 | —COC(CH₃)=CH₂ | 3-CH₂ | 1 | H | 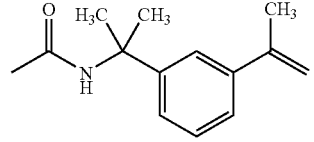 |
| 34 | 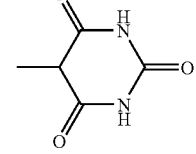 | 4-CH₂CH₂— | 1 | H | 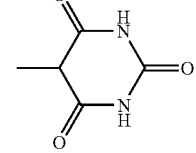 |
| 35 | —COC(CH₃)=CH₂ | 2-CH₂CH₂— | 1 | H | 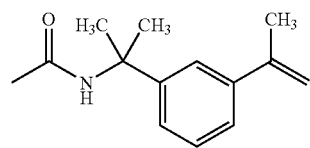 |

TABLE II

Ethylenically-unsaturated Yellow Azo Compounds

| Example No. | Q | B | L |
|---|---|---|---|
| 36 | —COC(CH₃)CH=CH₂ | 2-CONH— | —CH₂CH₂— |
| 37 | —COC(CH₃)CH=CH₂ | 3-CONH— | —CH₂CH(CH₃)— |
| 38 | —COC(CH₃)CH=CH₂ | 4-CONH— | —CH₂CH(CH₃)— |
| 39 | —COC(CH₃)CH=CH₂ | 3,5-di-CONH— | —CH₂C(CH₃)₂CH₂— |
| 40 | —COCH=CH₂ | 2-CONH— | —CH₂C(CH₃)₂CH₂— |
| 41 | | 2-CONH— | —(CH₂CH₂O)₂CH₂CH₂— |

TABLE II-continued

Ethylenically-unsaturated Yellow Azo Compounds $(Q-O-L-B)_m$ — phenyl ring (positions 1-6, with R at position 2) — $N=N-Z$

| # | (first substituent) | position | linker |
|---|---|---|---|
| 42 | —COCH(CH₃)=CH₂ | 2-CONH— | —CH₂CH(OC(O)C(CH₃)=CH₂)CH₂— |
| 43 | —COCH(CH₃)=CH₂ | 2-CONH— | —CH₂CH₂OCH₂CH₂— |
| 44 | —COCH(CH₃)=CH₂ | 2-CONH— | —CH₂CH(CH₃)— |
| 45 | —COCH(CH₃)=CH₂ | 4-O— | —CH₂CH₂— |
| 46 | —COCH(CH₃)=CH₂ | 4-O— | —CH₂CH₂OCH₂CH₂— |
| 47 | CH₃C(O)NH—C(CH₃)₂—(3-isopropenylphenyl) | 2-O— | —CH₂CH₂— |
| 48 | CH₃C(O)NH—C(CH₃)₂—(3-isopropenylphenyl) | 3-CONH— | —CH₂C(CH₃)₂CH₂— |
| 49 | CH₃C(O)NH—C(CH₃)₂—(3-isopropenylphenyl) | 4-O— | —(CH₂CH₂O)₂CH₂CH₂— |
| 50 | —COC(CH₃)=CH₂ | 2-CONH— | —CH₂CH₂— |
| 51 | —COCH=CH₂ | 4-CONH— | —CH₂CH(CH₃)— |
| 52 | CH₃C(O)NH—C(CH₃)₂—(3-isopropenylphenyl) | 3-CONH— | —(CH₂)₆— |
| 53 | —CONHCH₂CH₂OCOC(CH₃)=CH₂ | 3,5-di-CONH— | —CH₂CH₂OCH₂CH₂— |
| 54 | —CONHCOC(CH₃)=CH₂ | 2-CONH— | —(CH₂CH₂O)₂CH₂CH₂— |
| 55 | —COC(CH₃)₂NHCOC(CH₃)=CH₂ | 2-O— | —CH₂CH₂— |
| 56 | —COC(CH₃)=CH₂ | 4-O— | —CH₂CH(CH₃)— |
| 57 | CH₃C(O)NH—C(CH₃)₂—(3-isopropenylphenyl) | 2,4-di-O— | —CH₂CH₂— |
| 58 | —COCH=CHCO₂CH₃ | 2-S— | —CH₂CH₂CH₂— |
| 59 | —COCH=CH—CH₃ | 4-S— | —(CH₂)₄— |
| 60 | —COCH=CHC₆H₅ | 3-N(SO₂CH₃)— | —CH₂CH₂— |

TABLE II-continued

Ethylenically-unsaturated Yellow Azo Compounds $$(Q-O-L-B)_m \underset{5}{\overset{4}{\bigcirc}} \underset{6}{\overset{R}{\underset{1}{\bigcirc}}} \underset{N=N-Z}{\overset{2}{\underset{1}{\bigcirc}}}$$

| # | Q-O-L-B | R | Z |
|---|---|---|---|
| 61 | (furan-2-yl-CH=CH-CO-CH3 structure) | 4-N-(SO$_2$C$_6$H$_5$)— | —CH$_2$CH$_2$CH$_2$— |
| 62 | (thien-2-yl-CH=CH-CO-CH3 structure) | 3-O— | —CH$_2$CH(CH$_2$Cl)— |
| 63 | (4-acetylphenyl-maleimide structure) | 2,4-di-S— | —CH$_2$CH$_2$— |
| 64 | (4-acetyl-styrene structure) | 2,5-di-CONH— | —CH$_2$CH(CH$_3$)— |
| 65 | —COC(CH$_3$)=CH$_2$ | 2,4-di-CONH— | —CH$_2$CH$_2$— |
| 66 | —COCH=CH$_2$ | 2-CONH— | —CH$_2$CH(C$_6$H$_5$)— |
| 67 | —COC(CH$_3$)=CH$_2$ | 2-CONH— | —CH$_2$CH(CH$_3$)— |
| 68 | —COC(CH$_3$)=CH$_2$ | 2-CONH— | —CH$_2$CH(CH$_3$)— |
| 69 | —COC(CH$_3$)=CH$_2$ | 2-CONH | —CH$_2$CH(CH$_3$)— |
| 70 | —COC(CH$_3$)=CH$_2$ | 4-O— | —CH$_2$CH(CH$_3$)— |
| 71 | —COC(CH$_3$)=CH$_2$ | 3-CONH— | —CH$_2$CH$_2$— |
| 72 | —COC(CH$_3$)=CH$_2$ | 2,4-di-O— | —CH$_2$CH$_2$CH$_2$— |
| 73 | —COC(CH$_3$)=CH$_2$ | 3,5-di-CONH— | —CH$_2$CH(CH$_3$)— |
| 74 | (acetamido-dimethyl-isopropenylphenyl structure) | 4-CONH— | —CH$_2$CH(CH$_3$)— |
| 75 | (acetamido-dimethyl-isopropenylphenyl structure) | 3-O— | —CH$_2$CH(CH$_3$)— |
| 76 | (acetamido-dimethyl-isopropenylphenyl structure) | 3-CON(CH$_3$)— | —CH$_2$CH$_2$— |
| 77 | (acetamido-dimethyl-isopropenylphenyl structure) | 4-CON(CH$_3$)— | —CH$_2$CH$_2$OCH$_2$CH$_2$— |
| 78 | —COC(CH$_3$)=CH$_2$ | 2-CONH— | —CH$_2$CH(CH$_3$)— |
| 79 | —COC(CH$_3$)=CH$_2$ | 2-CONH— | —CH$_2$CH(CH$_3$)— |

TABLE II-continued

Ethylenically-unsaturated Yellow Azo Compounds $$(Q-O-L-B)_m \underset{5\quad 6}{\overset{4\quad 3\quad 2}{\text{phenyl}}}-N=N-Z$$

(with R at position 3, and N=N—Z at position 1)

| | | | |
|---|---|---|---|
| 80 | —COC(CH₃)=CH₂ | 2-CONH— | —CH₂CH(CH₃)— |
| 81 | Q—O—L—B— = Hydrogen | Q—O—L—B— = Hydrogen | Q—O—L—B— = Hydrogen |
| 82 | Q—O—L—B— = Hydrogen | Q—O—L—B— = Hydrogen | Q—O—L—B— = Hydrogen |
| 83 | Q—O—L—B— = Hydrogen | Q—O—L—B— = Hydrogen | Q—O—L—B— = Hydrogen |
| 84 | Q—O—L—B— = Hydrogen | Q—O—L—B— = Hydrogen | Q—O—L—B— = Hydrogen |

| Example No. | m | R | Z |
|---|---|---|---|
| 36 | 1 | H | 4-methyl-3-(4-methylphenyl)-1H-pyrazol-5(4H)-one substituent (N—C₆H₄-4-CH₃) |
| 37 | 1 | H | 4-methyl-3-methyl-1-phenyl-pyrazol-5(4H)-one (N—C₆H₅) |
| 38 | 1 | H | 4-methyl-3-methyl-1-methyl-pyrazol-5(4H)-one (N—CH₃) |
| 39 | 2 | H | 4-methyl-3-methyl-1-(2-acetoxyethyl)-pyrazol-5(4H)-one |
| 40 | 1 | H | 4-methyl-3-methyl-1-(2-methacryloyloxyethyl)-pyrazol-5(4H)-one |
| 41 | 1 | H | 4-methyl-3-phenyl-1-phenyl-pyrazol-5(4H)-one (H₅C₆ at 3-position, N—C₆H₅) |

TABLE II-continued
Ethylenically-unsaturated Yellow Azo Compounds
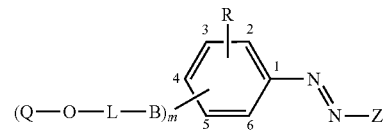
| | | | |
|---|---|---|---|
| 42 | 1 | H | 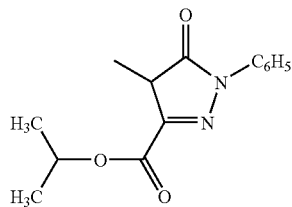 |
| 43 | 1 | 4-Cl | 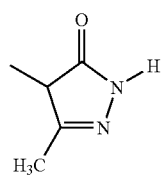 |
| 44 | 1 | H | 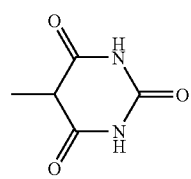 |
| 45 | 1 | H | 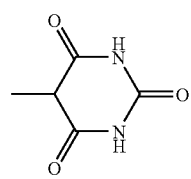 |
| 46 | 1 | H | 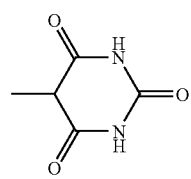 |
| 47 | 1 | H | 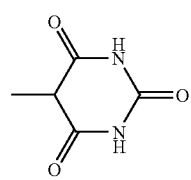 |
| 48 | 1 | H | 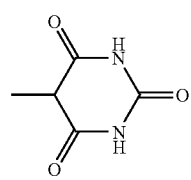 |

TABLE II-continued

Ethylenically-unsaturated Yellow Azo Compounds $(Q-O-L-B)_m$ — phenyl ring (positions 1-6, with R at position 2) — N=N—Z

| # | position | R | Z |
|---|---|---|---|
| 49 | 1 | H | 5-methylbarbituric acid group (pyrimidine-2,4,6-trione with methyl at C5) |
| 50 | 1 | H | —CH(COCH$_3$)CONHC$_6$H$_5$ |
| 51 | 1 | H | —CH(CH$_3$)(COCH$_3$)CONH(2-methylphenyl) |
| 52 | 1 | H | —CH(CH$_3$)(COCH$_3$)CONH(2-chlorophenyl) |
| 53 | 2 | H | —CH(CH$_3$)(COCH$_3$)CONH(4-methoxyphenyl) |
| 54 | 1 | H | —CH(CH$_3$)(COCH$_3$)CONH(2,4-dimethylphenyl) |
| 55 | 1 | H | —CH(CH$_3$)(COCH$_3$)CONH(4-chlorophenyl) |
| 56 | 1 | H | —CH(CH$_3$)(COCH$_3$)CONHC$_6$H$_5$ |

TABLE II-continued
Ethylenically-unsaturated Yellow Azo Compounds
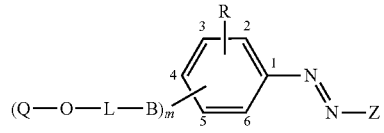
| | | R | Z |
|---|---|---|---|
| 57 | 2 | H | 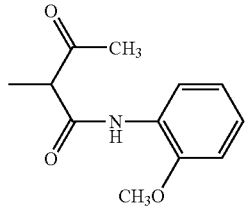 |
| 58 | 1 | H | —CH(COCH$_3$)CONH$_2$ |
| 59 | 1 | H | —CH(COCH$_3$)CONHCH$_2$CH$_3$ |
| 60 | 1 | H | —CH(COCH$_3$)CONHC$_6$H$_{11}$ |
| 61 | 1 | H | —CH(COCH$_3$)CONH-n-C$_4$H$_9$ |
| 62 | 1 | H | 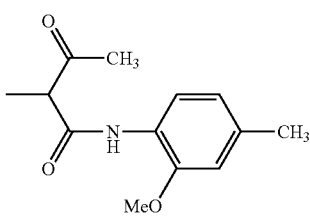 |
| 63 | 1 | H | 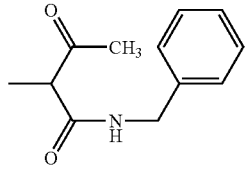 |
| 64 | 2 | H | 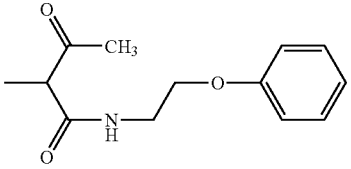 |
| 65 | 2 | H | 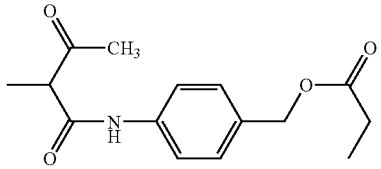 |
| 66 | 1 | H | 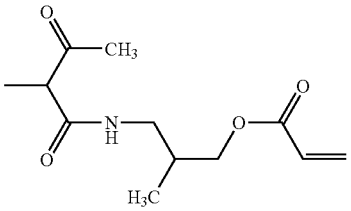 |
| 67 | 1 | 2,4-di-Cl | —CH(COC$_6$H$_5$)$_2$ |
| 68 | 1 | H | —CH(COCH$_3$)COC$_6$H$_5$ |

TABLE II-continued
Ethylenically-unsaturated Yellow Azo Compounds
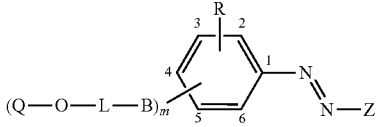
| | | | |
|---|---|---|---|
| 69 | 1 | H | 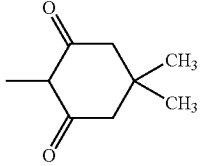 |
| 70 | 1 | H | 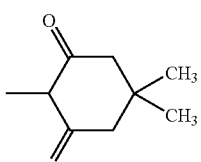 |
| 71 | 1 | H | 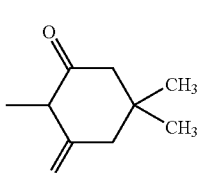 |
| 72 | 1 | H | 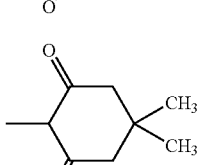 |
| 73 | 1 | H | 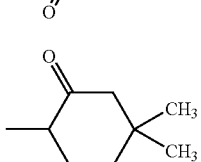 |
| 74 | 1 | H | 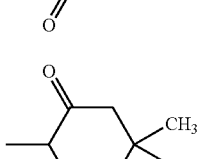 |
| 75 | 1 | H | —CH(COCH$_3$)$_2$ |
| 76 | 1 | H | —CH(COCH$_3$)COCH(CH$_3$)$_2$ |
| 77 | 1 | H | 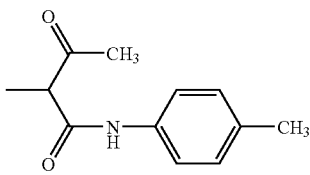 |
| 78 | 1 | H | —CH(CONH$_2$)$_2$ |
| 79 | 1 | H | —CH(CONHCH$_3$)$_2$ |
| 80 | 1 | H | —CH(CONHC$_6$H$_5$)$_2$ |
| 81 | O | 2-CO$_2$CH$_3$ | —CH(CONHC$_2$H$_4$OCOC(CH$_3$)=CH$_2$)$_2$ |

TABLE II-continued

Ethylenically-unsaturated Yellow Azo Compounds $$(Q-O-L-B)_m \underset{5\phantom{aa}6}{\overset{3\phantom{aa}2}{\underset{\phantom{a}}{\bigcirc}}} \overset{R}{\underset{1}{\phantom{aa}}} -\underset{N}{\overset{N}{\underset{\parallel}{}}}-Z$$

| | | | |
|---|---|---|---|
| 82 | O | 4-CO$_2$CH$_3$ | —CH(CONHC$_6$H$_4$-4-CH$_2$CH$_2$OCOCH=CH$_2$)$_2$ |
| 83 | O | 2-CO$_2$CH(CH$_3$)$_2$ | [structure] |
| 84 | O | 2-CO$_2$CH$_2$CH(C$_2$H$_5$)C$_4$H$_9$-n | [structure] |

Preparation of Lens Material

Example 85

Preparation of Stock Monomer Mixture

A stock mixture (50 g) of monomers suitable for preparing intraocular lens material is prepared by thoroughly mixing 2-phenylethyl acrylate (66 weight percent, PEA, CAS# 3530-36-7), 2-phenylethyl methacrylate (30.5 weight percent, PEMA, CAS# 3683-12-3) and 1,4-butanediol diacrylate (3.5 weight percent, BDDA, CAS# 1070-70-8).

Example 86

Control

To a 20 mL vial are added 10 g of the stock mixture and 2,2'-azobisisobutyronitrile (52.3 mg, CAS#78-67-1, thermal initiator) then mixed until a solution was obtained. About 2 g of the resulting solution are added to an 18 mm×150 mm test tube using a syringe. Polymerization is initiated by heating the test tube to 65° C. in a vacuum oven under nitrogen for 17 h then heating to 100° C. for an additional 3 h. The tubes are removed from the oven and allowed to cool to room temperature. The resulting polymer is removed using a spatula. The polymer is placed in a vial containing about 25 mL of acetone and crushed into small pieces using a spatula. The polymer pieces are placed into a Soxhlet extractor and extracted with refluxing acetone for 4 to 5 h. The polymer is removed, allowed to dry on a watch glass overnight and dried at 50° C. in a vacuum oven at a pressure of about 15 mm of Hg for 1 h. The resulting polymer is analyzed by ultraviolet-visible light spectroscopy.

Example 87

To a 20 mL vial is added 10.7 mg of the yellow polymerizable compound of Example 1b and 10 g of the stock mixture to give an azo concentration of about 0.1 weight percent. The mixture is stirred with gentle heating (about 50° C.) until a solution is obtain and allowed to cool to room temperature. A thermal polymerization initiator, 2,2'-azobisisobutyronitrile (52.3 mg, CAS#78-67-1), is added and mixed until a solution is obtained. About 2 g of the resulting solution are added to an 18 mm×150 mm test tube using a syringe. Polymerization is initiated by heating the test tube to 65° C. in a vacuum oven under nitrogen for 17 h then heating to 100° C. for an additional 3 h. The tubes are removed from the oven and allowed to cool to room temperature. The resulting polymer is removed using a spatula. The polymer is placed in a vial containing about 25 mL of acetone and crushed into small pieces using a spatula. The polymer pieces are placed into a Soxhlet extractor and extracted with refluxing acetone for 4 to 5 h. No color is observed in the Soxhlet vessel indicating that the azo compound is polymerized with the monomers during polymerization. The polymer is removed, allowed to dry on a watch glass overnight then dried at 50° C. in a vacuum over at a pressure of about 15 mm of Hg for 1 h. The resulting yellow polymer is analyzed by ultraviolet-visible light spectroscopy.

All patents, publications and abstracts cited above are incorporated herein by reference in their entirety provided that to the extent any definitions in such patents, publications, and abstracts conflict with those in the present application, the definitions herein shall control with respect to the text herein and each conflicting definition in a patent, publication, or abstract shall control with respect to the content of the document containing such conflicting definitions. It should be understood that the foregoing relates only to preferred embodiments of the present invention and that numerous modifications or alterations can be made therein without departing from the spirit and the scope of the present invention as defined in the following claims.

What is claimed is:

1. A polymer comprising at least one residue of a molecule comprising a molecular structure depicted by Formula I:

A—N=N—Z    I wherein A is an optionally substituted aryl radical and Z is the residue of a moiety selected from 2-pyrazolin-5-ones, dimedone (5,5-dimethyl-1,3-cyclohexanedione), acetoacetamides, malonamides, barbituric acid and 1,3-propanediones;

with the provision that when Z is 2-pyrazolin-5-one, A is selected from

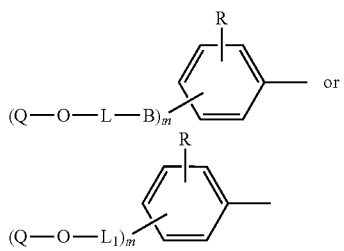

wherein

B is selected from —CON($R_1$)—, —O—, —S—, and —N($SO_2R_2$)—;

L is selected from $C_2$-$C_8$-alkylene and —[$CH_2CH(R_3)O$]$_n$—$CH_2CH(R_3)$—;

$L_1$ is a $C_1$-$C_8$-alkylene group;

m is selected from 0, 1 and 2;

n is 1, 2, or 3;

R is hydrogen or one to three groups selected from $C_1$-$C_8$-alkyl, $C_1$-$C_8$-alkoxy, halogen, cyano, nitro, thiocyano, trifluoromethyl, —$COR_4$, —$CO_2R_5$, —$SO_2R_2$, —N($R_1$)$COR_4$, —N($R_1$)$SO_2R_2$, arylazo, aryloxy, arylthio, heteroarylthio, —$SO_2N(R_1)R_4$, —$CON(R_1)R_4$, succinimido, phthalimido, and phthalimidino;

$R_1$ is selected from hydrogen, $C_1$-$C_8$-alkyl, $C_3$-$C_8$-cycloalkyl, $C_3$-$C_8$-alkenyl and aryl;

$R_2$ is selected from $C_1$-$C_8$-alkyl, $C_3$-$C_8$-cycloalkyl and aryl;

$R_3$ is hydrogen or methyl;

$R_4$ is selected from $C_1$-$C_8$-alkyl, $C_3$-$C_8$-cycloalkyl, aryl and hydrogen;

$R_5$ is selected from $C_1$-$C_8$-alkyl, $C_3$-$C_8$-cycloalkyl, aryl and [$CH_2CH(R_3)O$]$_n$$CH_2CH(R_3)OR_6$;

$R_6$ is selected from hydrogen, $C_1$-$C_8$-alkyl, aryl, $C_1$-$C_8$-alkanoyloxy and $C_1$-$C_8$-alkoxycarbonyloxy; and Q is an ethylenically-unsaturated polymerizable group selected from;

1a —COC($R_9$)=CH—$R_{10}$,

2a —CONHCOC($R_9$)=CH—$R_{10}$,

3a —CONH—$C_1$-$C_8$-alkylene-OCOC($R_9$)=CH—$R_{10}$,

4a —COC($R_{11}$)($R_{12}$)—NHCOC($R_9$)=C(H)—$R_{10}$,

5a —COCH=CH—$CO_2R_{13}$,

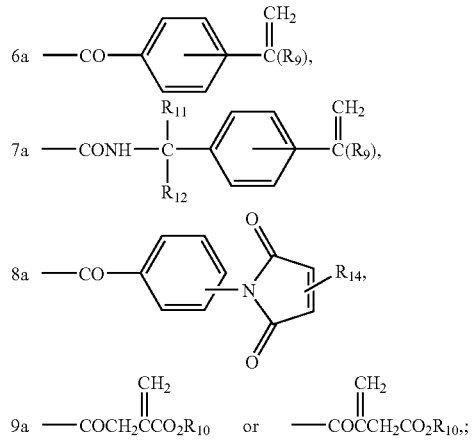

wherein:

$R_9$ is hydrogen or $C_1$-$C_8$ alkyl;

$R_{10}$ is hydrogen; $C_1$-$C_8$-alkyl; phenyl; phenyl substituted with one or more groups selected from $C_1$-$C_8$-alkyl, $C_1$-$C_8$-alkoxy, —N($C_1$-$C_8$-alkyl)$_2$, nitro, cyano, $C_1$-$C_8$-alkoxycarbonyl, $C_1$-$C_8$-alkanoyloxy and halogen; 1- or 2-narhthyl; 1- or 2-narhthyl substituted with $C_1$-$C_8$-alkyl or $C_1$-$C_8$-alkoxy: 2- or 3-thienyl: 2- or 3-thienyl substituted with $C_1$-$C_8$-alkyl or halogen; 2- or 3-furyl; or 2- or 3-furyl substituted with $C_1$-$C_8$-alkyl $R_{11}$ and $R_{12}$ are, independently, hydrogen, $C_1$-$C_8$-alkyl, or aryl; or $R_{11}$ and $R_{12}$ are combined to rerresent a ($CH_2$)$_{3-5}$- radical;

$R_{13}$ is hydrogen, $C_1$-$C_8$-alkyl, $C_3$-$C_8$-alkenyl, $C_3$-$C_8$-cycloalkyl or aryl: and $R_{14}$ is hydrogen, $C_1$-$C_8$-alkyl or aryl; and wherein the molecule comprises at least one ethylenically-unsaturated polymerizable group (Q), wherein when Z does not comprise at least one Q group, then m is 1 or 2.

2. A composition comprising the polymer of claim 1.

3. An article comprising the polymer of claim 1.

4. A method of making a polymer, comprising copolymerizing monomers wherein the monomers comprise a compound having the structure of Formula I:

A—N=N—Z    I wherein:

A is an optionally substituted aryl radical;

Z is the residue of a moiety selected from 2-pyrazolin-5-ones, dimedone (5,5-dimethyl-1,3-cyclohexanedione), acetoacetamides, malonamides, barbituric acid and 1,3-propanediones; with the provision that when Z is 2-pyrazolin-5-one, A is selected from:

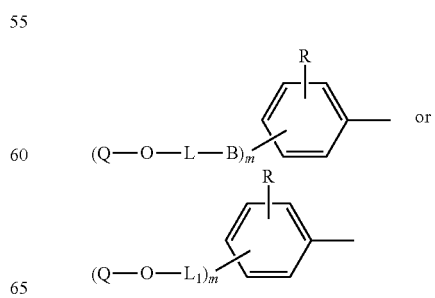

wherein

B is selected from —CON(R$_1$)—, —O—, —S—, and —N(SO$_2$R$_2$)—;

L is selected from C$_2$-C$_8$-alkylene and —[CH$_2$CH(R$_3$)O]$_n$—CH$_2$CH(R$_3$)—;

L$_1$ is a C$_1$-C$_8$-alkylene group;

m is selected from 0, 1 and 2;

n is 1, 2, or 3;

R is hydrogen or one to three groups selected from C$_1$-C$_8$-alkyl, C$_1$-C$_8$-alkoxy, halogen, cyano, nitro, thiocyano, trifluoromethyl, —COR$_4$, —CO$_2$R$_5$, —SO$_2$R$_2$, —N(R$_1$)COR$_4$, —N(R$_1$)SO$_2$R$_2$, arylazo, aryloxy, arylthio, heteroarylthio, —SO$_2$N(R$_1$)R$_4$, —CON(R$_1$)R$_4$, succinimido, phthalimido, and phthalimidino;

R$_1$ is selected from hydrogen, C$_1$-C$_8$-alkyl, C$_3$-C$_8$-cycloalkyl, C$_3$-C$_8$-alkenyl and aryl;

R$_2$ is selected from C$_1$-C$_8$-alkyl, C$_3$-C$_8$-cycloalkyl and aryl;

R$_3$ is hydrogen or methyl;

R$_4$ is selected from C$_1$-C$_8$-alkyl, C$_3$-C$_8$-cycloalkyl, aryl and hydrogen;

R$_5$ is selected from C$_1$-C$_8$-alkyl, C$_3$-C$_8$-cycloalkyl, aryl and [CH$_2$CH(R$_3$)O]$_n$CH$_2$CH(R$_3$)OR$_6$;

R$_6$ is selected from hydrogen, C$_1$-C$_8$-alkyl, aryl, C$_1$-C$_8$-alkanoyloxy and C$_1$-C$_8$-alkoxycarbonyloxy; and Q is an ethylenically-unsaturated polymerizable group selected from;

1a —COC(R$_9$)=CH—R$_{10}$,

2a —CONHCOC(R$_9$)=CH—R$_{10}$,

3a —CONH—C$_1$-C$_8$-alkylene-OCOC(R$_9$)=CH—R$_{10}$,

4a —COC(R$_{11}$)(R$_{12}$)—NHCOC(R$_9$)=C(H)—R$_{10}$,

5a —COCH=CH—CO$_2$R$_{13}$,

6a —CO—C$_6$H$_4$—C(R$_9$)=CH$_2$,

7a —CONH—C(R$_{11}$)(R$_{12}$)—C$_6$H$_4$—C(R$_9$)=CH$_2$,

8a —CO—C$_6$H$_4$—N(maleimide-R$_{14}$),

9a —COCH$_2$CCO$_2$R$_{10}$ or —COCCH$_2$CO$_2$R$_{10}$;

wherein:

R$_9$ is hydrogen or C$_1$-C$_8$ alkyl;

R$_{10}$ is hydrogen; C$_1$-C$_8$-alkyl; phenyl; phenyl substituted with one or more groups selected from C$_1$-C$_8$-alkyl, C$_1$-C$_8$-alkoxy, —N(C$_1$-C$_8$-alkyl)$_2$, nitro, cyano, C$_1$-C$_8$-alkoxycarbonyl, C$_1$-C$_8$-alkanoyloxy and halogen; 1- or 2-narhthyl; 1- or 2-narhthyl substituted with C$_1$-C$_8$-alkyl or C$_1$-C$_8$-alkoxy: 2- or 3-thienyl: 2- or 3-thienyl substituted with C$_1$-C$_8$-alkyl or halogen; 2- or 3-furyl; or 2- or 3-furyl substituted with C$_1$-C$_8$-alkyl R$_{11}$ and R$_{12}$ are, independently, hydrogen, C$_1$-C$_8$-alkyl, or aryl; or R$_{11}$ and R$_{12}$ are combined to rerresent a —(CH$_2$)$_{3-5}$- radical;

R$_{13}$ is hydrogen, C$_1$-C$_8$-alkyl, C$_3$-C$_8$-alkenyl, C$_3$-C$_8$-cycloalkyl or aryl: and R$_{14}$ is hydrogen, C$_1$-C$_8$-alkyl or aryl; and wherein the molecule comprises at least one ethylenically-unsaturated polymerizable group (Q), wherein when Z does not comprise at least one Q group, then m is 1 or 2.

5. The method of claim 4 wherein A is:

$$(Q-O-L-B)_m-C_6H_3(R)- \text{ or } (Q-O-L_1)_m-C_6H_3(R)-$$

wherein

B is a divalent linking group selected from —CON(R$_1$)—, —O—, —S—, and —N(SO$_2$R$_2$)—;

L is selected from C$_2$-C$_8$-alkylene and —[CH$_2$CH(R$_3$)O]$_n$—CH$_2$CH(R$_3$)—;

L$_1$ is a C$_1$-C$_8$-alkylene group;

m is selected from 0, 1 and 2;

n is 1, 2, or 3;

R is hydrogen or one to three groups selected from C$_1$-C$_8$-alkyl, C$_1$-C$_8$-alkoxy, halogen, cyano, nitro, thiocyano, trifluoromethyl, —COR$_4$, —CO$_2$R$_5$, —SO$_2$R$_2$, —N(R$_1$)COR$_4$, —N(R$_1$)SO$_2$R$_2$, arylazo, aryloxy, arylthio, heteroarylthio, —SO$_2$N(R$_1$)R$_4$, —CON(R$_1$)R$_4$, succinimido, phthalimido, phthalimidino;

R$_1$ is selected from hydrogen, C$_1$-C$_8$-alkyl, C$_3$-C$_8$-cycloalkyl, C$_3$-C$_8$-alkenyl and aryl;

R$_2$ is selected from C$_1$-C$_8$-alkyl, C$_3$-C$_8$-cycloalkyl and aryl;

R$_3$ is hydrogen or methyl;

R$_4$ is selected from C$_1$-C$_8$-alkyl, C$_3$-C$_8$-cycloalkyl, aryl and hydrogen;

R$_5$ is selected from C$_1$-C$_8$-alkyl, C$_3$-C$_8$-cycloalkyl, aryl and [CH$_2$CH(R$_3$)O]$_n$CH$_2$CH(R$_3$)OR$_6$;

R$_6$ is selected from hydrogen, C$_1$-C$_8$-alkyl, aryl, C$_1$-C$_8$-alkanoyloxy and C$_1$-C$_8$-alkoxycarbonyloxy;

Q is an ethylenically-unsaturated polymerizable group;

wherein, when Z does not comprise at least one Q group, then m is one or two.

6. The method of claim 4 wherein Z is a residue of a structure selected from:

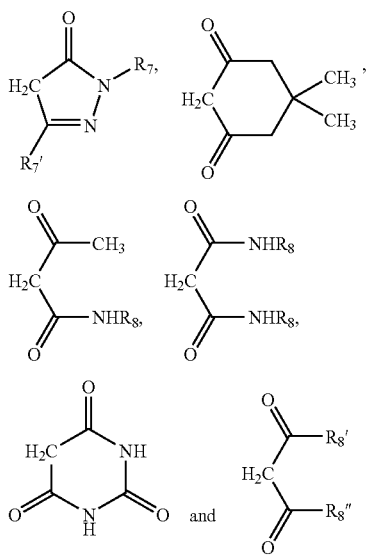

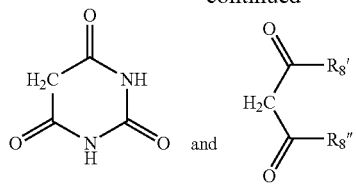

wherein:

$R_7$ is selected from hydrogen, $C_1$-$C_8$-alkyl, $C_3$-$C_8$-cycloalkyl, aryl, arylene-(B-L-O-Q)$_p$, arylene-(L$_1$-O-Q)$_p$ and —$C_2$-$C_8$-alkylene-O-Q;

$R_7'$ is selected from $C_1$-$C_8$-alkyl, trifluoromethyl, $C_3$-$C_8$-cycloalkyl, $C_1$-$C_8$-alkoxycarbonyl and aryl;

$R_8$ is hydrogen, $C_1$-$C_8$-alkyl, -L$_1$-O-Q, $C_3$-$C_8$-cycloalkyl, heteroaryl, aryl or aryl substituted with one to three groups selected from $C_1$-$C_8$-alkyl, $C_1$-$C_8$-alkoxy, halogen, —B-L-O-Q and L$_1$-O-Q;

$R_8'$ and $R_8''$ are independently selected from $C_1$-$C_4$-alkyl and aryl;

P is one or two;

B is a divalent linking group selected from —CON(R$_1$)—, —O—, —S—, and —N(SO$_2$R$_2$)—;

L is selected from $C_2$-$C_8$-alkylene and —[CH$_2$CH(R$_3$)O]$_n$—CH$_2$CH(R$_3$)—;

L$_1$ is a $C_1$-$C_8$-alkylene group; and n is selected from the one to three.

7. The method of claim 5 wherein Z is a residue of a structure selected from:

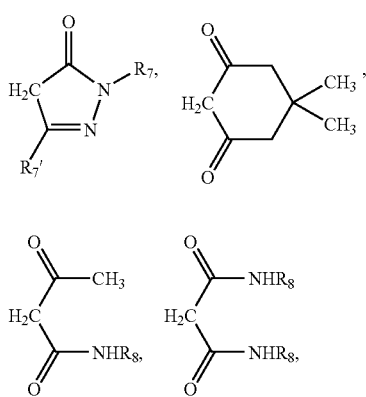

wherein $R_1$ is selected from hydrogen, $C_1$-$C_8$-alkyl, $C_3$-$C_8$-cycloalkyl, $C_3$-$C_8$-alkenyl and aryl;

$R_2$ is selected from $C_1$-$C_8$-alkyl, $C_3$-$C_8$-cycloalkyl and aryl;

$R_3$ is hydrogen or methyl;

$R_7$ is selected from hydrogen, $C_1$-$C_8$-alkyl, $C_3$-$C_8$-cycloalkyl, aryl, arylene-(B-L-O-Q)$_p$, arylene-(L$_1$-O-Q)$_p$ and —$C_2$-$C_8$-alkylene-O-Q;

$R_7'$ is selected from $C_1$-$C_8$-alkyl, trifluoromethyl, $C_3$-$C_8$-cycloalkyl, $C_1$-$C_8$-alkoxycarbonyl and aryl;

$R_8$ is hydrogen, $C_1$-$C_8$-alkyl, -L$_1$-O-Q, $C_3$-$C_8$-cycloalkyl, heteroaryl, aryl or aryl substituted with one to three groups selected from $C_1$-$C_8$-alkyl, $C_1$-$C_8$-alkoxy, halogen, —B-L-O-Q and L$_1$-O-Q;

$R_8'$ and $R_8''$ are independently selected from $C_1$-$C_4$-alkyl and aryl;

p is one or two;

B is a divalent linking group selected from —CON(R$_1$)—, —O—, —S—, and —N(SO$_2$R$_2$)—;

L is selected from $C_2$-$C_8$-alkylene and —[CH$_2$CH(R$_3$)O]$_n$—CH$_2$CH(R$_3$)—;

L$_1$ is a $C_1$-$C_8$-alkylene group; and n is selected from the one to three.

8. The method of claim 4 wherein A has the structure of Formula XIII:

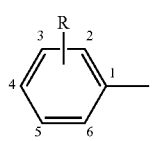

XIII wherein

R is hydrogen or one or two groups selected from $C_1$-$C_4$-alkyl, $C_1$-$C_4$-alkoxy, halogen, nitro, cyano and —CO$_2$C$_1$-C$_8$-alkyl, —CONHC$_1$-C$_8$-alkyl and —SO$_2$C$_1$-C$_4$-alkyl;

Z is a residue of:

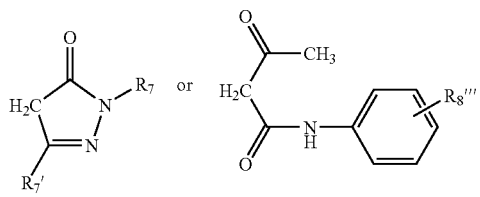

wherein $R_7$ is: —CH$_2$CH$_2$—O-Q,

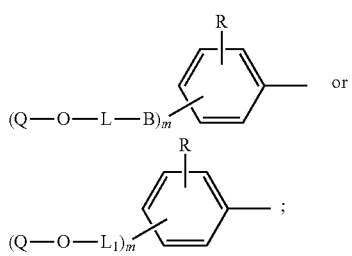

R$_7$' is selected from C$_1$-C$_4$-alkyl and aryl;
R$_8$''' is —B-L-O-Q or -L$_1$-O-Q;
B is —O—;
L is selected from C$_2$-C$_8$-alkylene and —[CH$_2$CH(R$_3$)O]$_n$—CH$_2$CH(R$_3$)—;
n is an integer from one to three;
R$_3$ is hydrogen or methyl;
L$_1$ is C$_1$-C$_8$-alkylene; and
Q is selected from

—COC(R$_9$)=CH—R$_{10}$ or

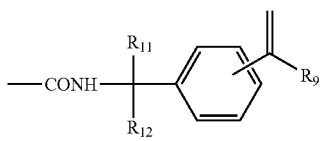

wherein
R$_9$ is hydrogen or methyl;
R$_{10}$ is hydrogen; and
R$_{11}$ and R$_{12}$ are methyl.

9. The method of claim 8 wherein R is:
a —CO$_2$C$_1$-C$_8$-alkyl group or a nitro group attached to the 2-position carbon in Formula XIII; wherein when nitro is attached to the 2-position a C$_1$-C$_4$-alkyl, a C$_1$-C$_4$-alkoxy or a halogen is optionally attached to the 4-position carbon in Formula XIII.

10. The method of claim 4, wherein A is:

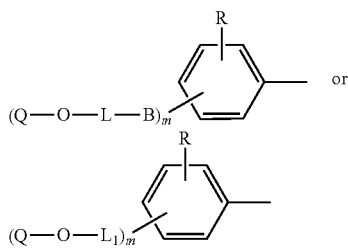

wherein
R is hydrogen;
B is —O— or —CONH—;
L is C$_2$-C$_8$-alkylene or —[CH$_2$CH(R$_3$)O—]$_n$CH$_2$CH(R$_3$)—;
L$_1$ is C$_1$-C$_8$-alkylene;
R$_3$ is hydrogen or methyl;
n is 1, 2, or 3;
m is 1; and Z is a residue of:

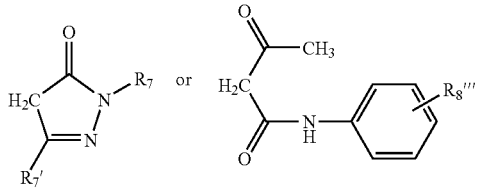

wherein
R$_7$ is hydrogen, C$_1$-C$_4$-alkyl or aryl;
R$_7$' is C$_1$-C$_4$-alkyl or aryl;
R$_8$''' is hydrogen or one to three groups selected from C$_1$-C$_4$-alkyl, C$_1$-C$_4$-alkoxy and halogen; and
Q is:

—COC(R$_9$)=CH—R$_{10}$ or

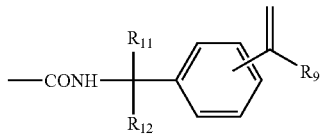

wherein
R$_9$ is hydrogen or methyl;
R$_{10}$ is hydrogen; and
R$_{11}$ and R$_{12}$ are methyl.

11. The method of claim 10, wherein A is:

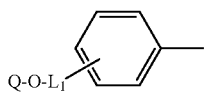

wherein
L$_1$ is C$_1$-C$_8$-alkylene;
Z is the residue of:

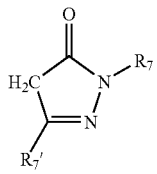

wherein
R$_7$ is hydrogen, C$_1$-C$_4$-alkyl or aryl;
R$_7$' is C$_1$-C$_4$-alkyl or aryl;
Q is:

—COC(R$_9$)=CH—R$_{10}$ wherein
R$_9$ is hydrogen or methyl; and
R$_{10}$ is hydrogen.

12. The polymer of claim 1, wherein if Q is —COC(R$_9$)=CH—R$_{10}$ then A is not

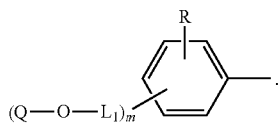

13. The method of claim 4, wherein if Q is —COC(R$_9$)=CH—R$_{10}$ then A is not

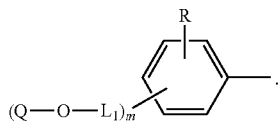

14. The method of claim 5, wherein if Q is —COC(R$_9$)=CH—R$_{10}$ then A is not

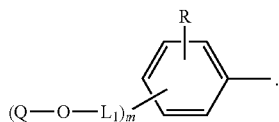

15. The method of claim 6, wherein if Q is —COC(R$_9$)=CH—R$_{10}$ then A is not

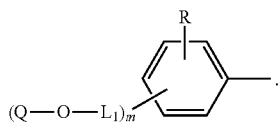

16. The method of claim 7, wherein if Q is —COC(R$_9$)=CH—R$_{10}$ then A is not

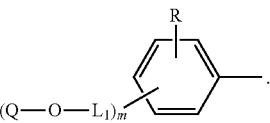

17. The method of claim 8, wherein if Q is —COC(R$_9$)=CH—R$_{10}$ then A is not

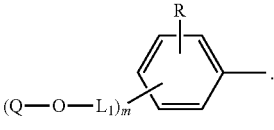

18. The method of claim 9, wherein if Q is —COC(R$_9$)=CH—R$_{10}$ then A is not

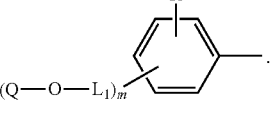

19. The method of claim 10, wherein if Q is —COC(R$_9$)=CH—R$_{10}$ then A is not

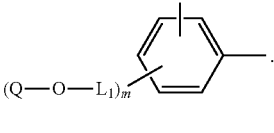

20. A composition comprising the polymer of claim 12.
21. An article comprising the polymer of claim 12.

* * * * *